(12) United States Patent
Numano et al.

(10) Patent No.: US 9,789,149 B2
(45) Date of Patent: Oct. 17, 2017

(54) VEGETATION WATER COMPOSITION FOR TREATMENT OF INFLAMMATORY SKIN CONDITIONS

(75) Inventors: Fujio Numano, Tokyo (JP); Roberto Crea, San Mateo, CA (US); Tokuko S. Wiedemann, El Cerrito, CA (US); Catherine M. Bitler, Menlo Park, CA (US)

(73) Assignee: CreAgri, Inc., Hayward, CA (US)

( * ) Notice: Subject to any disclaimer, the term of this patent is extended or adjusted under 35 U.S.C. 154(b) by 0 days.

(21) Appl. No.: 11/185,246

(22) Filed: Jul. 19, 2005

(65) Prior Publication Data

US 2007/0020350 A1    Jan. 25, 2007

(51) Int. Cl.
*A61K 36/63*    (2006.01)
*A61K 9/20*    (2006.01)
*A61K 31/05*    (2006.01)

(52) U.S. Cl.
CPC ............ *A61K 36/63* (2013.01); *A61K 9/2059* (2013.01); *A61K 31/05* (2013.01)

(58) Field of Classification Search
CPC ..... A61K 31/00; A61K 2236/00; A61K 36/63
USPC .................................. 424/777, 769; 514/27
See application file for complete search history.

(56) References Cited

U.S. PATENT DOCUMENTS

| | | | |
|---|---|---|---|
| 4,370,274 A | 1/1983 | Finch et al. | |
| 4,452,744 A | 6/1984 | Finch et al. | |
| 4,522,119 A | 6/1985 | Finch et al. | |
| 5,059,431 A | 10/1991 | Daeschel et al. | |
| 5,714,150 A | 2/1998 | Nachman | |
| 5,719,129 A | 2/1998 | Andary et al. | |
| 5,998,641 A | 12/1999 | Ganguli et al. | |
| 6,117,844 A | 9/2000 | Fredrickson | |
| 6,162,480 A | 12/2000 | van Buuren et al. | |
| 6,165,475 A * | 12/2000 | Crea et al. | 424/769 |
| 6,197,308 B1 * | 3/2001 | Crea et al. | 424/769 |
| 6,358,542 B2 | 3/2002 | Cuomo et al. | |
| 6,361,803 B1 | 3/2002 | Cuomo et al. | |
| 6,416,808 B1 * | 7/2002 | Crea | 426/601 |
| 6,437,004 B1 * | 8/2002 | Perricone | 514/738 |
| 6,440,465 B1 | 8/2002 | Meisner | |
| 6,682,763 B2 | 1/2004 | Kuno et al. | |
| 6,743,449 B2 | 6/2004 | Pinnell et al. | |
| 6,746,706 B1 | 6/2004 | van der Boom et al. | |
| 6,936,287 B1 * | 8/2005 | Crea et al. | 424/769 |
| 7,261,909 B2 | 8/2007 | Crea | |
| 7,713,569 B2 | 5/2010 | Crea | |
| 8,216,599 B2 | 7/2012 | Crea | |
| 2002/0004077 A1 | 1/2002 | Cuomo et al. | |
| 2002/0198415 A1 | 12/2002 | Crea | |
| 2003/0108651 A1 | 6/2003 | Crea | |
| 2003/0113392 A1 | 6/2003 | Theoharides | |
| 2003/0185921 A1 | 10/2003 | Fotinos et al. | |
| 2004/0039066 A1 * | 2/2004 | Crea | 514/731 |
| 2005/0103711 A1 | 5/2005 | Emmons et al. | |
| 2005/0158798 A1 | 7/2005 | Sher | |
| 2006/0257351 A1 | 11/2006 | Chiba | |
| 2007/0084797 A1 | 4/2007 | Cooper et al. | |
| 2008/0026100 A1 | 1/2008 | Villa et al. | |
| 2008/0090000 A1 | 4/2008 | Crea | |
| 2008/0300198 A1 | 12/2008 | Matt et al. | |
| 2010/0216874 A1 | 8/2010 | Crea | |
| 2011/0257117 A1 | 10/2011 | Matt et al. | |
| 2014/0011756 A1 | 1/2014 | Crea | |

FOREIGN PATENT DOCUMENTS

| | | |
|---|---|---|
| AU | 8858001 | 3/2002 |
| AU | 2003211118 | 9/2003 |
| AU | 2008249142 | 12/2008 |
| AU | 2008249142 | 8/2012 |
| AU | 2006269843 | 4/2013 |
| CA | 2474798 | 12/2012 |
| CN | 1646093 | 7/2005 |
| EP | 0295722 | 12/1988 |
| EP | 0 581 748 | 7/1993 |
| EP | 0855908 | 8/1998 |
| EP | 1230926 | 8/2002 |
| EP | 1482909 | 12/2004 |
| EP | 1924269 | 5/2008 |
| EP | 1924269 | 3/2015 |
| ES | 2006904 | 5/1989 |
| HK | 1071694 | 7/2005 |
| IT | 1276576 | 11/1997 |
| IT | 1278025 | 11/1997 |
| JP | 07-223940 | 8/1995 |
| JP | 08-119825 | 5/1996 |
| JP | 09-078061 | 3/1997 |
| JP | 2001-181197 | 7/2001 |
| JP | 2001-181632 | 7/2001 |

(Continued)

OTHER PUBLICATIONS

Kobayashi et al.: An Alternative Approach to Atopic Dermatitis: Part I—Case Serires Presentation. eCAM 2004 (1; (1) 49-62.*
Rutledge. Anti-Inflammatories. Dermatology Times. Oct. 2003. vol. 24 Issue 10. pp. 1-4 of Proquest.*
Stibich et al. Papular Uriticaria. Cutis. Aug. 2001. vol. 68. Iss. 2, pp. 1-3 of Proquest.*
umm.edu. Herbal Medicine. Retrieved from the internet on Jan. 30, 2011 <http://www.umm.edu/altmed/articles/herbal-medicine-000351.htm>. 9 pages.*
Amalfitano, G., Commission of the European Communities, Luxemborg pp. 145-150 OSTI of DE910018386 Conference: Energy Innovation and the Agro-Food Industry (Abstract) (1990).
Aziz et al., "Comparative Antibacterial and Antifungal Effects of Some Phenolic Compounds", *Microbios*, 93:43-54 (1998).

(Continued)

*Primary Examiner* — Chris R Tate
*Assistant Examiner* — Deborah Davis
(74) *Attorney, Agent, or Firm* — Carr & Ferrell LLP

(57) ABSTRACT

Compositions obtained from vegetation water from olives and methods for treating patients suffering from an inflammatory skin disease with the compositions are described. Included are hydroxytyrosol rich compounds obtained from olive vegetation water.

12 Claims, 12 Drawing Sheets

(56) References Cited

FOREIGN PATENT DOCUMENTS

| | | |
|---|---|---|
| JP | 2005517033 | 6/2005 |
| JP | 2005366391 | 4/2006 |
| JP | 2008509224 | 3/2008 |
| JP | 2009502805 | 1/2009 |
| JP | 5466403 | 1/2014 |
| KR | 1020040084913 | 10/2004 |
| KR | 1020087004638 | 4/2008 |
| NZ | 534884 | 5/2007 |
| NZ | 534884NZ | 9/2007 |
| WO | WO9721434 | 6/1997 |
| WO | WO 97/28089 | 8/1997 |
| WO | WO97/39632 | 10/1997 |
| WO | WO9747711 | 12/1997 |
| WO | WO0036936 | 6/2000 |
| WO | WO 01/76579 | 10/2001 |
| WO | WO 01/76579 A1 * 10/2001 ............. A61K 31/05 |
| WO | WO 02/18310 A1 * 3/2002 ............. C07C 39/11 |
| WO | WO 03/032966 | 4/2003 |
| WO | WO 03/068171 | 8/2003 |
| WO | WO03068171 | 8/2003 |
| WO | WO2006020588 | 2/2006 |
| WO | WO2007012057 | 1/2007 |

OTHER PUBLICATIONS

Bonina, F. et al., Biofenoli Dell'ulivo, *Cosm. Technol.*, (No English translation available). 2131:18-22 (1999).

Braga et al., "Olive Oil, Other Seasoning Fats, and the Risk of Colorectal Carcinoma", *American Cancer Society*, 82:448-453 (1998).

Bruner et at, "A Systematic Review of Adverse Effects Associated with Topical Treatments for Psoriasis", *Dermatology Online Journal*, 9(1)2, 2003.

D'Amicis, A. and Farchi, S., "Olive Oil Consumption and Cancer Mortality in Italy", *Advances in Nutrition and Cancer 2* (Zappia, V., et al., Eds.) 67-72, Kluwer Academic/Plenum Publishers, New York (1999).

De La Puerta et al., "Inhibition of Leukocyte 5-Lipoxygenase by Phenolics from Virgin Olive Oil", *Biochemical Pharmacology*, 57:445-449 (1999).

Deiana et al., "Inhibition of Peroxynitrite Dependent DNA Base Modification and Tyrosine Nitration by the Extra Virgin Olive Oil-Derived Antioxidant Hydroxytyrosol", *Free Radical. Biology and Medicine*, 26:762-769 (1999).

Feletar et al., "Treatment of Refractory Psoriatic Arthritis with Infliximab: A 12 Month Observational Study of 16 Patents", *Ann. Rheum Dis.*, 63:156-161 (2004).

Ficarra et al. "HPLC Analysis of Oleuropein and Some Flavonoids in Leaf and Bud of *Olea europaea* L.", *Fasrmaco*, 46(6):803-815 (1991).

Fleming et al., "Isolation of a Bacterial Inhibitor From Green Olives", *Applied Microbiology*, 18(5):856-860 (1969).

Ho, V.C., "The Use of Ciclosporin in Psoriasis: A Clinical Review," *Br. J. Dermatology*, 150(Suppl. 67):1-10 2004.

Kohyama et al., Inhibition of Arachidonate Lipoxygenase Activities by 2-(3,4-Dihydroxyphenol)ethanol, a Phenolic Compound Olives, *Biosci. Biotech. Biochem.*, 61(2):347-350 (1997).

Koutsoumanis et al. "Modeling the Effectiveness of a Natural Antimicrobial on *Salmonella enteritidis* as a Function of Concentration, Temperature and pH, Using Conductance Measurements", *Journal of Applied Microbiology*, 84:981-987 (1998).

Lebwohl et al., "Psoriasis Treatment: Traditional Therapy", *Ann. Rheum Dis*, 64(Suppl. 2):ii83-ii86 (2005).

Limiroli et al., "$^1$H NMR Study of Phenoloics in the Vegetation Water of Three Cultivars of *Olea europaea*: Similarities and Differences", *Journal of Agricultural and Food Chemistry*, 44(8):2040-2048 (Abstract) (1996).

Manna et al., "Transport Mechanism and Metabolism of Olive Oil Hydroxytyrosol in CAco-2 Cells", *FEBS Letters*, 470:341-344 (2000).

Marchetti et al., "Treatments for Mild-To-Moderate Recalcitrant Plaque Psoriasis: Expected Clinical and Economic Outcomes for First-Line and Second-Line Care", *Dermatology Online Journal*, 11(1):1-11 (2005).

Martin-Moreno et al., "Dietary Fat, Olive Oil Intake and Breast Cancer Risk" *Int J. Cancer*, 58:774-780 (1994).

Mason and Krueger, "Thioguanine for Refractory Psoriasis: A 4-Year Experience", *J. Am. Acad. Dermatol.*, 44(6):67-72 (2001).

Mattson, F.H. and Grundy, S.M., "Comparison of Effects of Dietary Saturated, Mono-unsaturated, and Poly-unsaturated Fatty Acids on Plasma Lipids and Lipoproteins in Man", *J. Lipid Res.* 26:194-202 (1985).

Owen, R.W., et al., "The Identification of Lignans As Major Components of the Phenolic Fraction of Olive Oil" *J. Can. Res. Clin. Onc.*, 125:S31 (Abstract K22) (2000).

Owen, R.W., et al., "The Antioxidant/Anticancer Potential of Phenolic Compounds Isolated From Olive Oil", *Eur. J. Cancer*, 36:1235-1247 (2000).

Owen, R.W., et al., "Phenolic Compounds and Squalene in Olive Oils: The Concentration and Antioxidant Potential of Total Phenols, Simple Phenols, Secoiridoids, Lignans and Squalene", *Food Chemical Toxicology*, 38:647-659 (2000).

Parthasarathy, S., et al., "Low Density Lipoprotein Rich in Oleic Acid is Protected Against Oxidative Modification: Implications for Dietary Prevention of Atherosclerosis", *Proc. Natl. Acad. Sci. USA*, 87:3894-3898 (1990).

Petroni, A., et al., "Inhibition of Platlet Aggregation and Eicosanoid Production by Phenolic Components of Olive Oil", *Thrombosis Research*, 78(2):151-160 (1995).

Rifai et al., "Inflammatory Markers and Coronary Heart Disease", *Curr. Opin. Lipidol.*, 13:383-389 (2002).

Risch, H.A., et al., "Dietary Fat Intake and Risk of Epithelial Ovarian Cancer", *Journal of the National Cancer Institute*, 86:1409-1415 (1994).

Psoriasis, $2^{nd}$ Ed., Roenigk and Maibach eds. $2^{nd}$ ed. New York Marcel Deker, 213-214 (1991).

Romani, A., et al., Polyphenolic Content in Five Tuscany Cultivars of *Olea europaea* L., *J. Agric. Food Chem.*, 47:964-967 (1999).

Saija et al., "In Vitro Evaluation of the Antioxidant Activity and Biomembrane Interaction of the Plant Phenols Oleuropein and Hydroxytyrosol", *International Journal of Pharmaceutics*, 166:123-133 (1998).

Saija and Uccella, "Olive Biophenols: Functional Effects on Human Wellbeing", *Trends in Food Science & Technology*, 11(9-10):357-363 (2001).

Servili et al., "High-Performance Liquid Chromatography Evaluation of Phenols in Olive Fruit, Virgin Olive Oil, Vegetation Waters and Pomace and 1D- and 2D-Nuclear Magnetic Resonance Characterization", *Journal of the American Oil Chemists Society*, 76(7):873-882 (Abstract) (1999).

Tassou et al., "Inhibition of *Salmonella enteritidis* by Oleuropein in Broth and in a Model Food System", *Letters in. Applied Microbiology*, 20(2):120-124 (1995).

Tranter et al., "The Effect of the Olive Phenolic Compound, Oleuropein, on Growth and Enterotoxin B Production by *Staphylococcus aureus*", *Journal of Applied Bacteriology*, 74(3):253-259 (1993).

Tuck et al., "Major Phenolic Compounds in Olive Oil: Metabolism and Health Effects", *Journal of Nutritional Biochemistry*, 13:636-644 (2002).

Tsimidou, M., et al., "Determination of Phenolic Compounds in Virgin Olive Oil by reversed-Phase HPLC with Emphasis on UV Detection", *Food Chemistry*, 44:53-60 (1992).

Visioli et al., "Free Radical-Scavenging Properties of Olive Oil Polyphenols", *Biochemical and Biophysical Research Communications*, 247:60-64 (1998).

Visioli et al., "Oleuropein, the Bitter Principle of Olives, Enhances Nitic Oxide Production by Mouse Macrophages", *Life Sciences*, 62(6):541-546 (1998).

Visioli et al., "Waste Waters From Olive Oil Production are Rich in Natural Antioxidants" *Experimentia*, 51:32-34 (1995).

(56) References Cited

OTHER PUBLICATIONS

Visioli et al.. Olive Oils Rich in Natural Catecholic Phenols Decrease Isoprostane Excretion in Humans, *Biochemical and Biophysical Research Communications*, 278(3):797-799 (2000).
Ragione, F. et al., "Hydroxytyrosol, a natural molecule occurring in olive oil, induces cytochrome c-dependent apoptosis", *Biochemical and Biophysical Research Communications*, 278:733-739 (2000).
Visioli, F., "Antioxidant and other biological activities of olive mill waste waters", *J. Agric. Food Chem.*, 47(8):3397-3401 (1999).
Visioli, F., "Olive phenol hydroxytyrosol prevents passive smoking-induced oxidative stress", *Circulation*, 102:2169-2171 (2000).
Walter et al., "Preparation of Antimicrobial Compounds by Hydrolysis of Oleuropein from Green Olives", *Applied Microbiology*, 26(5):773-776 (1973).
Pratico et al., "Increased F2-isoprostanes in Alzheimer's disease: evidence for enhanced lipid peroxidation in vivo," FASEB Journal, 12 (15): 1777-1783, (1998).
Rice-Evans, "Plant polyphenols: free radical scavengers or chain-breaking antioxidants?," Biochem Society Symposium 61: 103-116, (1995).
Rimbach et al., "Methods to assess free radicals and oxidative stress in biological systems," Arch Anim Nutr., 52(3): 203-222, (1999).
Ryan et al., "Plasma Levels of Soluble CD14 and Tumor Necrosis Factor-alpha Type II Receptor Correlate with Cognitive Dysfunction during Human Immunodeficiency Virus Type 1 Infection," J Infect Dis 184: 699-706, (2001).
Sarkkinen et al., "Effects of two low-fat diets, high and low in polyunsaturated fatty acids, on plasma lipid peroxides and serum vitamin E levels in free-living hypercholesterolaemic men," Eur J Clin Nut., 47: 623-630, (1993).
Shi et al., "Dexamthasone Induces Hypertrophy of Developing Medial Septum Cholinergic Neurons: Potential Role of Nerve Growth Factor," J Neurosci 18(22): 9326-34, (1998).
Treitinger et al., "Decreased antioxidant defense in individuals infected by the human immunodeficiency virus," Eur J Clin Invest, 30(5): 454-459, (2000).
Visioli et al., "Antiatherogenic components of olive oil," Curr Atheroscler Rep 3(1 ): 64-67, (2001).
Le Tutour et al., "Antioxidant activities of Olea europaea leaves and related phenolic compounds," Phytochemistry, vol. 31, No. 4, pp. 1173-1178 (1992). Abstract only.
The First Official Action from the CN Patent Application No. 03815986.4 based on PCT/US2003/021111.
The Second Official Action from the CN Patent Application No. 03815986.4 based on PCT/US2003/021111.
The Third Official Action from the CN Patent Application No. 03815986.4 based on PCT/US2003/021111.
The Fourth Official Action from the CN Patent Application No. 03815986.4 based on PCT/US2003/021111.
The Fifth Official Action from the CN Patent Application No. 03815986.4 based on PCT/US2003/021111.
The Text of Rejection Decision from the CN Patent Application No. 03815986.4 based on PCT/US2003/021111.
The Notification of Allowance from the CN Patent Application No. 03815986.4 based on PCTI US2003/021111.
A First Report on Patent Application from the AU Patent Application No. 2003211118 dated Feb. 21, 2007 based on PCT/US2003/004761.
A First Report on Patent Application from the AU Patent Application No. 2008249142 dated Jan. 29, 2010 based on PCT/US2003/004761.
A Notice of Final Rejection from the JP Patent Application No. 2004-519909 dated Sep. 20, 2011 based on PCT/US2003/021111.
A Request for Amendment from the AU Patent Application No. 2003211118 dated Sep. 22, 2008 based on PCT/US2003/004761.
A Request for Amendment from the AU Patent Application No. 2008249142 dated Oct. 21, 2011 based on PCT/US2003/004761.
A Response to Official Action from the CA Patent Application No. 2474798 dated May 3, 2010 based on PCT/US2006/004761.
An Official Communication from the CA Patent Application No. 2474798 dated Nov. 3, 2009 based on PCT/US2006/004761.
A response to Official Action dated Feb. 16, 2010 for the AU Patent Application No. 2003249719 based on PCT/US2003/021111.
A response to Official Action dated Sep. 19, 2006 for the CN Patent Application No. 03815986.4 based on PCT/US2003/021111.1.
A Response to Official Communication from the EP Patent Application No. 03739832.8 dated Nov. 30, 2010 based on PCT/2006/004 761.
A response to the Official Action for the EP Patent Application No. 03763237.9 dated Feb. 9, 2010 based on PCT/US2003/021111.
A response to the EP Patent Office from the EP Patent Application No. 06788032.8 dated Feb. 1, 2010 based on PCT/US2006/028265.
A response to the Fifth Official Action for the CN Patent Application No. 03815986.4 based on PCT/US2003/021111.
A Second Report on Patent Application from the AU Patent Application No. 2003211118 dated Sep. 30, 2008 based on PCT/US2003/004761.
Amendments and Arguments from the JP Patent Application No. 2003-567356.4 based on PCT/US2006/004761.
An Amendment to the EP Patent Office from the EP Patent Application No. 06788032.8 dated Mar. 1, 2011 based on PCT/US2006/028265.
An Official Action from the AU Patent Application No. 2006269843 dated Mar. 11, 2011 based on PCT/US2006/028265.
An Official Action from the AU Patent Application No. 2003249719 dated Jun. 26, 2008 based on PCT/US2003/021111.
An Official Action dated Oct. 28, 2009 from the JP Patent Application No. 2004-519909 based on PCT/US2003/021111.
An Official Action from the CA Patent Application No. 2491613 dated Jul. 20, 2010 based on PCT/US2003/021111.
An Official Action from the EP Patent Application No. 03763237.9 dated Jul. 30, 2009 based on PCT/US2003/021111.
An Official Action from the JP Patent Application No. 2004-519909 dated Jun. 30, 2010 based on PCT/US2003/021111.
An Official Action from the JP Patent Application No. 2004-519909 dated Oct. 26, 2009 based on PCT/US2003/021111.
An Official Action from the KR Patent Application No. 10-2005-7000208 dated Nov. 24, 2009 based on PCT/US2003/021111.
An Official Communication from the EP Patent Application No. 03739832.8 dated Feb. 1, 2012 based on PCT/US2006/004761.
An Official Communication from the EP Patent Application No. 03739832.8 dated Feb. 12, 2010 based on PCT/US2006/004761.
An Official Communication from the EP Patent Application No. 06788032.8 dated Dec. 7, 2009 based on PCT/US2006/028265.
An Official Communication from the EP Patent Application No. 06788032.8 dated Sep. 27, 2011 based on PCT/US2006/028265.
An Official Communication from the IN Patent Application No. 308/MUMNP/2008 dated Sep. 21, 2011 based on PCT/US2006/028265.
Examination Report from the NZ Patent Application No. 534884 dated Jan. 17, 2007 based on PCT/US2006/004761.
Examination Report from the NZ Patent Application No. 534884 dated Nov. 22, 2005 based on PCT/US2006/004761.
First Office Action from the CN Patent Application No. 03803885.4 based on PCT/US2006/004761.
Notice of Final Rejection from the JP Patent Application No. 2003-567356.4 dated Jun. 15, 2010 based on PCT/US2006/004761.
Notice of Grounds for Rejection from the KR Patent Application No. 1 0-2004-7012613 dated Nov. 20, 2009 based on PCT/US2006/004761.
Ibbotson et al., "The Effects of Radicals Compared with UVB as Initiating Species for the Induction of Chronic Cutaneous Photodamage," The Journal of Investigative Dermatology, 1999.
Kiritsakis, "Flavor Components of Olive Oil—A Review," Journal of the American Oil Chemists' Society, vol. 75, No. 6, 1998.
Papadopoulos et al., "Antioxidant Effect of Natural Phenols on Olive Oil," Journal of the American Oil Chemists' Society, vol. 68, No. 9, Sep. 1991.
Papadopoulos et al., "Stability of Virgin Olive Oil: Assessment of Natural Antioxidants and Other Related Factors," Food Flavors, Ingredients and Composition, Charalambous, G., Ed., Elsevier, Amsterdam, pp. 321-326, (1993).

(56) References Cited

OTHER PUBLICATIONS

Tsimidou et al., "Phenolic Compounds and Stability of Virgin Olive Oil—Part I," 45 Food Chemistry, pp. 141-144, 1992.
Amari et al., "Olive Leaves: Their Extract Performs Effective Antiradicalic Action," 125 SOFW Journal, pp. 30-32, (1999).
Chimi et al., "Peroxyl and Hydroxyl Radical Scavenging Activity of Some Natural Phenolic Antioxidants," 68 Journal of American Oil Chemists' Society, No. 5, (1991).
Armstrong et al., "Environmental Factors and Cancer Incidence and Mortality in Different Countries, with Special Reference to Dietary Practices," 15 International Journal of Cancer, pp. 617-631 , (1975).
Bartsch et al., "Dietary Polyunsaturated Fatty Acids and Cancers of the Breast and Colorectum: Emerging for Their Role as Risk Modifiers," 20 Carcinogenesis, No. 12, pp. 2209-2218, (1999).
Capasso et al., "A Highly Convenient Synthesis of Hyroxytyrosol and Its Recovery from Agricultural Waste Waters," 47 Journal of Agricultural and Food Chemistry, No. 4, pp. 1745-1748, (1999).
Capasso et al., "Isolation Spectroscopy and Selective Phytotoxic Effects of Polyphenols From Vegetable Waste Waters," 31 Phytochemistry, No. 12, pp. 4125-4128, (1992).
Chan et al.,"What Causes Prostate Cancer? A Brief Summary of Epidemiology," 8 Seminars in Cancer Biology, pp. 263-273, (1998).
Gerber, "Epidemiology of Diet and Cancer, Olive Oil and Cancer," Chapter 13, pp. 263-275, edited by M.J. Hill, Ellis Horwood, New York, (1994).
Kuller et al., "Dietary Fat and Chronic Diseases: Epidemiologic Overview," 97 Journal of the American Dietetic Association, S9-S15, (1997).
La Vecchia et al., "Monounsaturated and other Types of Fat, and the Risk of Breast Cancer," 7 European Journal of Cancer Prevention, pp. 461-464, (1998).
Manna et al., "Biological effects of hyrdoxytyrosol, a polyphenol from olive oil endowed with antioxidant activity," 472 Advances in Experimental Medicine and Biology, pp. 115-130, (1999).
Owen et al., "Olive-oil Consumption and Health: the Possible Role of Antioxidants," Lancet Oncology, vol. 1, No. 2, pp. 107-112 (2000).
Pacific Health Services, "Olive Leaf Extract Product Information," Product Page Information (2006).
An Official Action dated Oct. 28, 2009 from JP Patent Application No. 2004-519909 based on PCT/US2003/021111.
Capasso et al., "Production of Hydroxytyrosol from Olive Oil Vegetation Waters," Agrochimica, vol. XXXVIII (1994).
Fehri et al., "*Olea europeaea* L.: Stimulant, anti-ulcer and anti-inflammatory effects," Boll. Chim. Farmaceutico, 135: 42-49 (1996).
Capasso et al., "Production of Glucose and Bioactive Aglycone by Chemical and Enzymatic Hydrolysis of Purified Oleuropein from Olea Europea," Appl. Biochem. and Biotech., vol. 61., pp. 365-377 (1996).
Benavente-Garcia et al., "Antioxidant activity of phenolics extracted from *Olea europaea* L. Leaves," J. Food Chem., vol. 68, pp. 457-462 (2000).
Duran et al., "Lactobacillus plantarum Survival During the First Days of Ripe Olive Brining," System. Appl. Microbiol., vol. 16, pp. 153-158 (1993).
Lazzerini et al., "Reduction of plasma homocysteine level in patients with rehumatoid arthritis given pulsed glucocorticoid treatment," Ann Rheum Dis., 62 694-695, Aug. 2001. see website article http://ard.bmj.com/content/62/7/694.full, accepted Dec. 2002).
Galli et al., "Antioxidant and Other Activities of Phenolics in Olives/Olive Oil, Typical Components of the Mediterranean Diet," Lipids, vol. 34, Supp. 1, pp. S23-S26 (1999).
Pinnaclife'S, Exhibit B Invalidity Contentions re: U.S. Pat. No. 6,416,808.
Visioli et al., "Olive Oil Phenolics are Dose-dependently Absorbed in Humans," FEBS Letters 468(2):159-160, (2000).
Visioli et al., "The effect of minor constituents of olive oil on cardiovascular disease: new findings," Nutr Rev., 56: 142-147, (1998).

International Search Report dated Oct. 10, 2003 from PCT/US03/21111; International Filing Date D Mar. 7, 2003.
Adamson et al., "Rate and severity of HIV-associated dementia (HAD): correlations with Gp41 and iNOS," Mol Med 5: 98-109, (1999).
Addis, P.B. et al., "Atherogenic and anti-atherogenic factors in the human diet," Biochem. Soc. Symp. 61: 259-271, (1995).
Caruso, D. et al., "Effect of virgin olive oil phenolic compounds on in vitro oxidation of human low density lipoproteins," Nutr Metab Cardiovascula Dis., 9(3): 102-107, (1999).
Cohen et al., "Neurocognitive performance enhanced by highly active antiretroviral therapy in HIV-infected women," AIDS, 15: 341-345, (2001).
Dal Pan et al., "Clinicopathologic correlations of HIV-1-associated vacuolar myelopathy: an autopsy-based case control study," Neurology 44: 2159-2164, (1994).
Dore et al., "Changes to AIDS dementia complex in the era of highly active antiretroviral therapy," AIDS 13: 1249-1253, (1999).
Ellis et al., "Cerebrospinal fluid human immunodeficiency virus type 1 RNA levels are elevated in neurocognitively impaired individuals with acquired immunodeficiency syndrome," HIV Neurobehavioral Research Center Group in Ann Neurol., 42: 679-688, (1997).
Enting et al., "Cerebrospinal fluid beta2-microglobulin, monocyte chemotactic protein-1, and soluble tumor necrosis factor alpha receptors before and after treatment with Lamivudine plus zivovudine or stavudine," Journal of Neuroimmunology, 102(2): 216-221, 2000.
Glass et al., "Microglia in HIV-associated neurological diseases," Microscopy Research and Technique 54: 95-105, 2001.
Glass et al., "Immunocytochemical quantitation of HIV virus in the brain: correlations with dementia," Annals of Neurology, vol. 38, No. 5, pp. 755-762, (1995).
Lipton et al., "Dementia Associated with the Acquired Immunodeficiency Syndrome," The New England Journal of Medicine, 332: 934-940, (1995).
Koutsilieri et al., "Neurotransmission in HIV Associated Dementia: a short review," Journal of Neural Transm., 108: 767-775, (2001).
Mazur et al., "Inhibitory effect of procyanidin-rich extracts on LDL oxidation in vitro," Atherosclerosis, 145: 421-422, (1999).
Masliah et al., "Changes in pathological findings at autopsy in AIDS cases for the last 15 years," AIDS 2000, 14: 69-74, (2000).
McArthur, "Neurologic manifestations of AIDS," Medicine 66: 407-437, (1987).
McGuire et al., "Pharmacologic frontiers in the treatment of AIDS dementia," J Psychopharmacology 14(3): 251-257, (2000).
Ng et al., "Anti-Human Immunodeficiency Virus (Anti-HIV) Natural Products with Special Emphasis on HIV Reverse Transcriptase inhibitors," Life Sciences, 61(10): 933-49, (1997).
Napoli et al., "Involvement of Oxidation-Sensitive Mechanisms in the Cardiovascular Effects of Hypercholesterolemia," Mayo Clin Proc, 76: 619-631, (2001).
Nottet et al., "Unraveling the neuroimmune mechanisms for the HI4:281-290V-1-associated cognitive/motor complex," Immunol Today 16(9): 441-448, (1995).
"Petito et al., ""Vacuolar myelopathy pathologically resembling subacute combined degeneration in patients with the acquired immunodeficiency syndrome,"" New England Journal of Medicine, 312: 874-879, (1985)."
Notice of Allowance dated Jun. 20, 2013, U.S. Appl. No. 12/776,812, filed May 10, 2010.
Non-Final Office Action dated May 26, 2011, U.S. Appl. No. 12/776,812, filed May 10, 2010.
Non-Final Office Action dated Dec. 8, 2010, U.S. Appl. No. 11/659,861, filed Apr. 10, 2008.
Final Office Action dated Oct. 11, 2013, U.S. Appl. No. 13/156,275, filed Jun. 8, 2011.
Non-Final Office Action dated Nov. 9, 2012, U.S. Appl. No. 13/156,275, filed Jun. 8, 2011.
Final Office Action dated Oct. 30, 2012, U.S. Appl. No. 13/544,943, filed Jul. 9, 2012.
Non-Final Office Action dated Apr. 24, 2013, U.S. Appl. No. 13/544,943, filed Jul. 9, 2012.

(56) References Cited

OTHER PUBLICATIONS

Notice of Reasons for Rejection from the JP Patent Application No. 2003-567356.4 dated May 22, 2009 based on PCT/US2006/004761.
Notification of Rejection from the CN Patent Application No. 03803885.4 dated Aug. 1, 2008 based on PCT/US2006/004761.
Response to Examination Report from the NZ Patent Application No. 534884 dated Dec. 15, 2006 based on PCT/US2006/004761.
Response to Examination Report from the NZ Patent Application No. 534884 dated Mar. 15, 2007 based on PCT/US2006/004761.
Response to Written Opinion and Amendments Under Article 34 from the International Application No. PCT/US2006/028265.
Shi et. al., "Neuronal apoptosis induced by HIV-1 Tat protein and TNF-alpha: potentiation of neurotoxicity mediated by oxidative stress and implications for HIV-1 dementia," J of NeuroVirology 4:281-290 (1998).
The Notification of Allowance dated Jan. 6, 2014 from the JP Patent Application No. 2008-522975 based on PCT PCT/US2006/028265.
Visioli et al., "Antioxidant and Other Biological Activities of Olive Mill Waste Waters," 47 Journal of Agricultural and Food Chemistry, No. 8, pp. 3397-34, (1999).
International Search Report and Written Opinion for PCT Application PCT/US2005/028179 dated Dec. 13, 2005.
Fujita et al., "Antioxidant activity of Hidrox," 53(1), 99-108 (2005).
Official Action from the EP Patent Application No. 06788032.8 dated Feb. 24, 2014 based on PCT/US2006/028265.
International Search Report and Written Opinion for PCT Application PCT/US2006/028265 dated Aug. 6, 2007.
International Search Report for PCT Application PCT/US2003/004761 dated Aug. 14, 2003.
European Search Report from the EP Patent Application No. 06788032.8 dated Nov. 18, 2009 based on PCT/US2006/028265.
Supplemental European Search Report from the Ep Patent Application No. 03739832.8 dated Jul. 3, 2007 based on PCT/US2003/004761.
Official Action from the EP Patent Application No. 06788032.8 dated Mar. 27, 2013 based on PCT/US2006/028265, 4 pages.
Official Action from the EP Patent Application No. 03739832.8 dated Feb. 16, 2015 based on PCT/US2003/004761, 4 pages.
Official Action from the EP Patent Application No. 03739832.8 dated Feb. 12, 2010 based on PCT/US2003/004761, 3 pages.
Official Action from the EP Patent Application No. 03739832.8 dated Feb. 1, 2012 based on PCT/US2003/004761, 5 pages.
Official Action from the NZ Patent Application No. 534884 dated Nov. 22, 2005 based on PCT/US2003/004761, 2 pages.
Office Action from the JP Patent Application No. 2007-525717 dated Oct. 3, 2011, 4 pages.
Exogeneous. Definition of Exogeneous by Medical dictionary. Http://medical-dictionary.thefreedictionary.com/Exogeneous. Sep. 2015, 3 pages.
European Patent Application No. 03739832.8, "Office Action," dated Feb. 14, 2017, 4 pages.
Choquenet et al., "Quercetin and Rutin as Potential Sunscreen Agents: Determination of Efficacy by an in Vitro Method," Journal of Natural Products, No. 71, 1117-1118 (2008).
Intention to Grant dated Jul. 8, 2014 in European Patent Application No. 06788032.8, filed Jul. 19, 2006.
A First Report on Patent Application from the AU Patent Application No. 2013202454 dated Jun. 3, 2014 based on PCT/US2006/028265.
Final Office Action dated Feb. 26, 2015, U.S. Appl. No. 12/776,812, filed May 10, 2010.
Non-Final Office Action dated Oct. 16, 2015, U.S. Appl. No. 12/776,812, filed May 10, 2010.
Final Office Action dated Feb. 10, 2016, U.S. Appl. No. 13/156,275, filed Jun. 8, 2011.
Non-Final Office Action dated Dec. 27, 2016, U.S. Appl. No. 13/156,275, filed Jun. 8, 2011.

\* cited by examiner

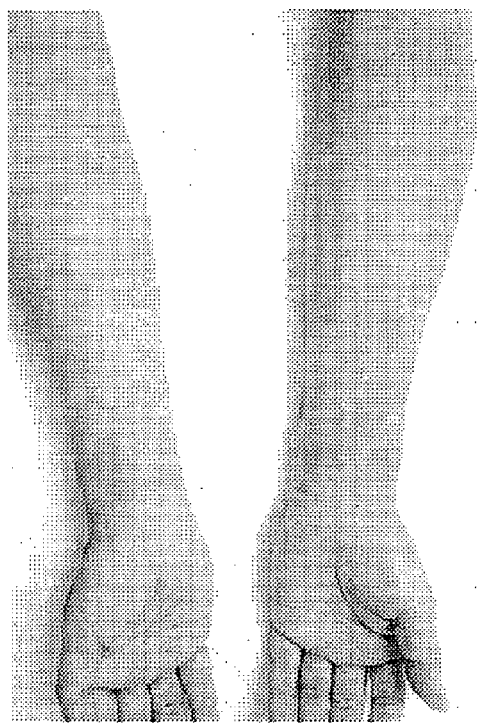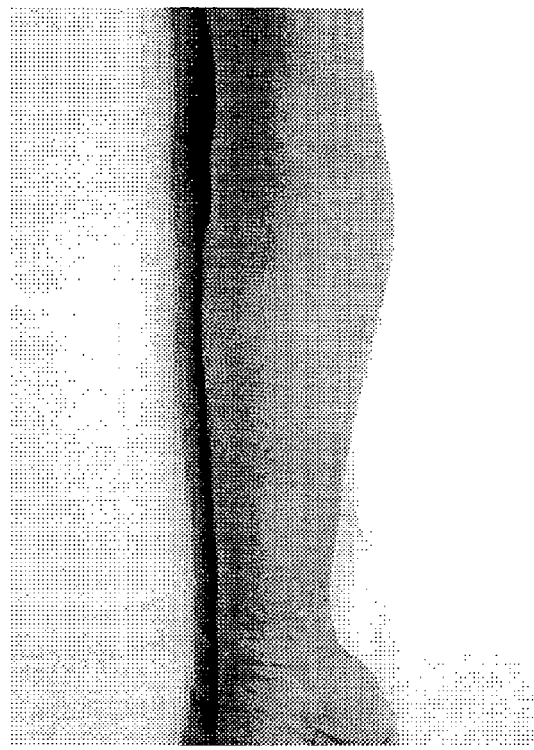
Fig. 2A  Fig. 2B
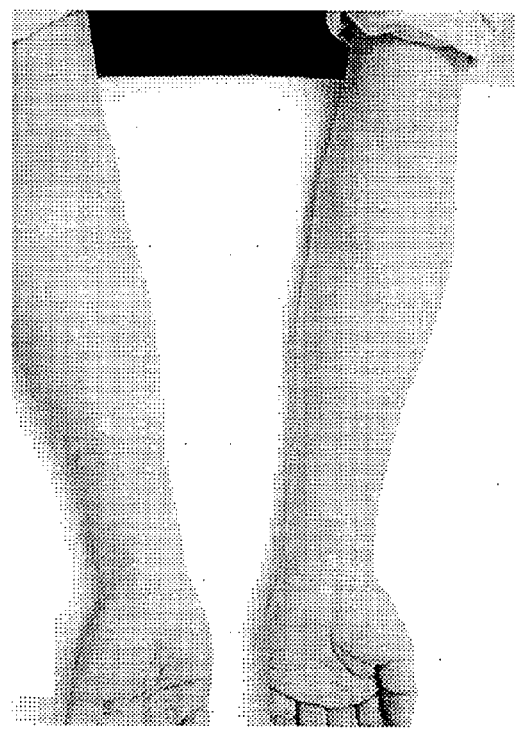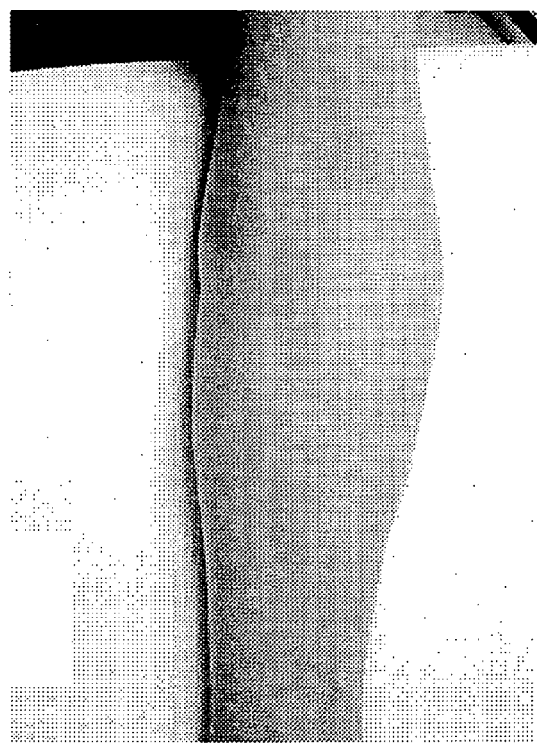
Fig. 2C  Fig. 2D

VEGETATION WATER COMPOSITION FOR TREATMENT OF INFLAMMATORY SKIN CONDITIONS

BACKGROUND

Olive oil, the principal fat component of the Mediterranean diet, has been associated with a lower incidence of coronary heart disease (Owen et al., 2000b; Parthasarathy et al., 1990; Mattson and Grundy, 1985) and certain cancers (d'Amicis and Farchi, 1999; Braga et al., 1998; Martin-Moreno et al., 1994). Several laboratories have reported that the hydrolysis of the olive oil phenolic oleuropin and other family members lead to small phenolic components with strong chemoprotective activity (Owen et al., 2000a; Manna et al., 2000). In particular, the olive oil phenolic hydroxytyrosol prevents low density lipoprotein (LDL) oxidation (Visioli and Galli, 1998), platelet aggregation (Petroni et al., 1995), and inhibits 5- and 12-lipoxygenases (de la Puerta et al., 1999; Kohyama et al., 1997). Hydroxytyrosol has also been found to exert an inhibitory effect on peroxynitrite dependent DNA base modification and tyrosine nitration (Deiana et al., 1999), and it counteracts cytotoxicity induced by reactive oxygen species in various human cellular systems (Manna et al., 2000). The use of hydroxytyrosol and oleuropein simple and polyphenols, respectively, obtained from olive oil have further been used for the treatment of skin damage (Perricone, U.S. Pat. No. 6,437,004). Finally, studies evaluating bioavailability have shown that hydroxytyrosol is dose-dependently absorbed in humans following ingestion (Visioli et al., 2000).

Conventionally, olive oil production involves crushing olives, including the pits, to produce a thick paste. During this procedure, the crushed olives are continuously washed with water, a process known as "malaxation." The paste is then mechanically pressed to squeeze out the oil content. In addition to providing olive oil, the pressing also squeezes out the paste's water content. Such washing and pressing steps yield a considerable amount of water, referred to as "vegetation water."

Both the pit and the pulp of olives are rich in water-soluble, phenolic compounds. Such compounds are extracted from olives during malaxation, according to their partition coefficients, and end up in the vegetation water. This explains why various phenolic compounds, such as oleuropein and its derivatives, produced in olive pulp, can be found in abundance in vegetation waters. Similarly, a number of monophenolic compounds, such as tyrosol and its derivatives, produced in olive pits, are also abundant in vegetation waters.

A hydroxytyrosol-rich composition from olive vegetation water may be prepared by adding acid to stabilize the vegetation water with the added benefit of preventing fermentation. In this manner, at least a portion of the oleuropein in the vegetation water is converted to hydroxytyrosol (Crea, U.S. Pat. No. 6,416,808 and related U.S. Publication No. 2003/0108651).

SUMMARY

In one aspect, a method for treating a person suffering from an inflammatory skin condition that has proven refractory to treatment with immunosuppressives or glucocorticoids is provided. In one embodiment, the method comprises orally administering a composition obtained from vegetation water from olives, where the amount administered is effective to produce a substantial improvement in the condition.

In one embodiment, the composition is administered on a daily basis. In another embodiment, the composition is administered over a period of at least one to two months or more.

In one embodiment, the composition is a hydroxytyrosol-rich composition produced by (i) producing vegetation water from olives, (ii) adding acid to the vegetation water thereby producing acidified vegetation water, and (iii) incubating the acidified vegetation water for a period until at least about 50% of oleuropein originally present in the vegetation water has been converted to hydroxytyrosol. In another embodiment, the composition is a hydroxytyrosol-rich composition produced by (i) producing vegetation water from olives, (ii) adding acid to the vegetation water thereby producing acidified vegetation water, and (iii) incubating the acidified vegetation water for a period until the weight ratio of hydroxytyrosol to oleuropein is between about 1:1 and about 200:1. In a further embodiment, the weight ratio is between about 5:1 and about 50:1

In embodiments, oral administration comprises orally administering a tablet, capsule, pill, or liquid.

The inflammatory skin condition may be one or more of psoriasis, eczema, allergic dermatitis, photohypersensitivity dermatosis, or lichen urticatus, among others.

In one embodiment, the composition is administered at a dosage effective to deliver between about 5.4 to 10.8 mg of total polyphenols daily. In another embodiment, the composition is administered at a dosage effective to deliver between about 2.5 to 5 mg of hydroxytyrosol daily.

The immunosuppressive may be selected from the group consisting of tacrolimus and/or hydroxyurea, among others known in the art.

BRIEF DESCRIPTION OF THE FIGURES

FIGS. 2A-2D are scanned images of the forearms and lower leg of a patient suffering from allergic dermatitis before (FIGS. 2A-2B) and after treatment (FIGS. 2C-2D);

DETAILED DESCRIPTION

All publications, patents, patent applications or other references cited in this application are herein incorporated by reference in their entirety as if each individual publication, patent, patent application or reference are specifically and individually indicated to be incorporated by reference.

I. Definitions

A "skin condition," "skin condition characterized by inflammation," or "inflammatory skin condition" as used herein refers to a skin condition characterized by any of redness, localized heat, swelling, pain, and/or itching.

The term "treatment" refers to inhibiting or arresting the development of a disease or condition in a patient, particularly a human, causing regression of the disease or condition, or relieving the symptoms associated with the disease or condition.

"Oral" refers to any route that involves administration by the mouth or direct administration into the stomach or intestines, including gastric administration.

"Psoriasis" refers to a chronic, immune-mediated inflammatory skin disease usually characterized by raised red skin covered by a flaky white buildup.

"Eczema" is an inflammation of the skin usually causing itching and may be accompanied by scaling or blisters.

Figure 7:
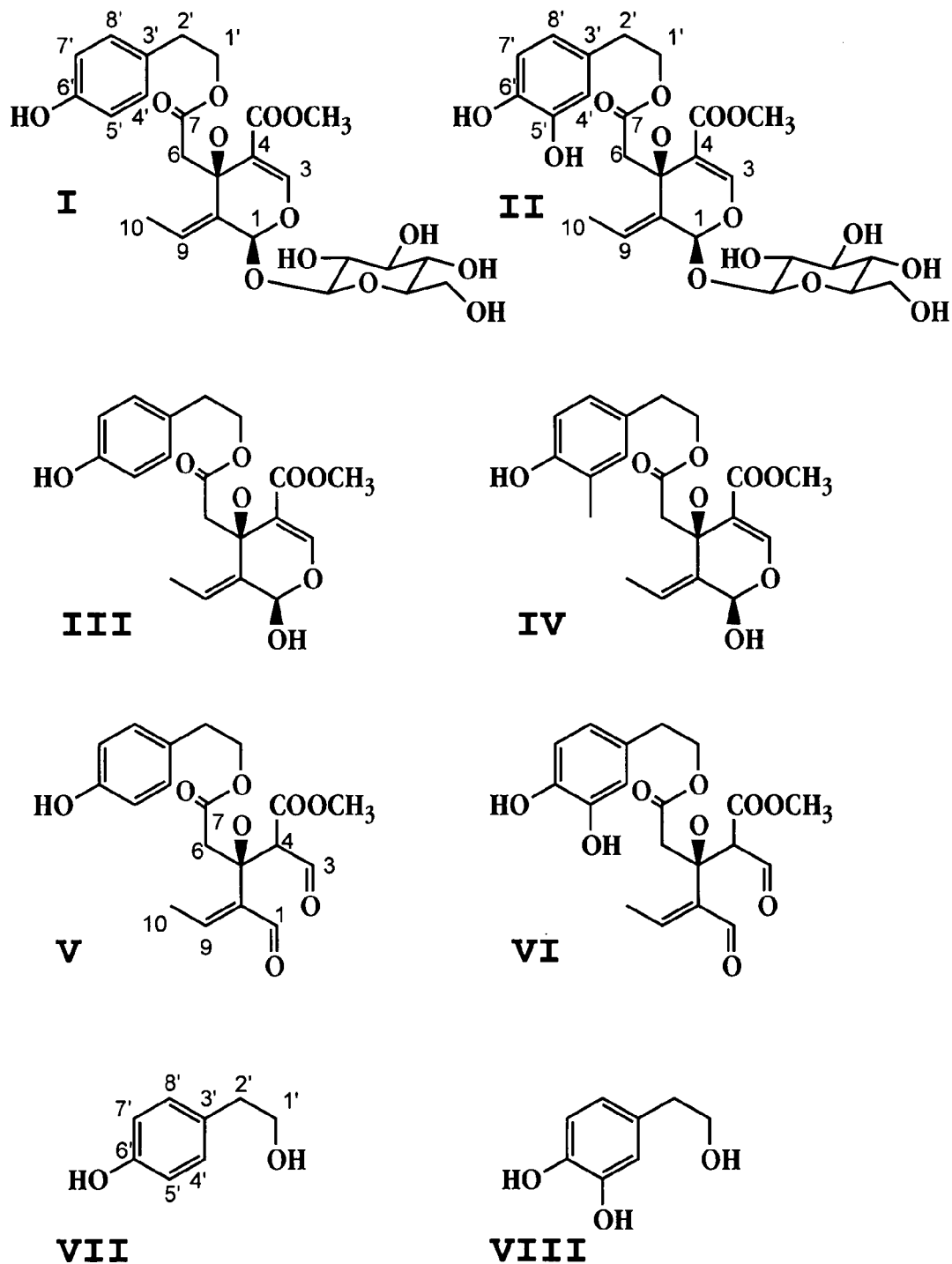
FIG. 7 shows the structures of phenolic compounds and their precursors detected in olive oil: ligstroside (I); oleuropein glucoside (II); aglycone of ligstroside (III); aglycone of oleuropein glucoside (IV); dialdehydic form of ligstroside aglycone lacking a carboxymethyl group (V); dialdehydic form of oleuropein glucoside aglycone lacking a carboxymethyl group (VI); tyrosol (VII); hydroxytyrosol (VIII).

"Oleuropein" refers to secoiridoid glucoside oleuropein (Structure II in FIG. 7). By "hydroxytyrosol" is intended 3,4-dihydroxyphenethyl alcohol (Structure VIII in the FIG. 7).

By "tyrosol" is intended 4-hydroxyphenethyl alcohol (Structure VII in FIG. 7).

II. Vegetation Water Composition

A. Vegetation Water Composition

In one aspect, the invention provides compositions for treating inflammatory skin conditions such as psoriasis or eczema.

The composition is obtained from vegetation water from olives. As illustrated below, this compound has been found to effectively reverse or reduce the symptoms of inflammatory skin conditions such as eczema and psoriasis, especially in cases previously refractory to treatment.

The olives may be obtained from conventional and commercially available sources such as growers. Preferably, the vegetation water is obtained from pitted olives. Pits in the olives contain tyrosol which is generally an undesired component in the vegetation water and which may not be appreciably broken down by the acid treatment described with reference to the hydroxytyrosol-rich composition described further below. The pits may be separated from the pulp manually or in an automated manner as described below. Preferably, such means should be capable of segregating the pits without breaking them, which might otherwise cause higher concentrations of tyrosol in the vegetation water. In another embodiment, the vegetation water is obtained from olives that have not been pitted.

To produce vegetation water, olive pulp from the olives is first pressed to obtain a liquid-phase mixture including olive oil, vegetation water, and solid by products. Thereafter, the vegetation water is separated from the rest of the liquid phase mixture and collected. Exemplary methods of obtaining vegetation water are described in co-owned U.S. Pat. Nos. 6,165,475 and 6,197,308, both of which are expressly incorporated herein by reference in their entirety.

For purposes of commercial production, it may be desirable to automate various aspects of the invention. In this regard, one embodiment contemplates the use of an apparatus as disclosed in U.S. Pat. Nos. 4,452,744, 4,522,119 and 4,370,274, each to Finch et al., and each expressly incorporated herein by reference. Briefly, Finch et al. teach an apparatus for recovering olive oil from olives. Initially, olives are fed to a pulper that separates the olive pits from the olives to obtain a pitless olive meat. The meat is then taken up by an extraction screw that subjects the meat to an extraction pressure sufficient to withdraw a liquid phase, comprising oil, water and a minor proportion of olive pulp. The liquid phase is collected in a bin and then sent to a clarifying centrifuge that separates the pulp from the liquid phase to obtain a mixture comprising olive oil and vegetation water. A purifying centrifuge may be used to separate the vegetation water and a small proportion of solid matter from the mixture.

Additional devices that may be used in practicing the present invention are disclosed in Italian Patent Nos. 1276576 and 1278025, each of which is expressly incorporated herein by reference. As above, these devices can be used to separate the pulp from the pits prior to processing of the crushed olive pulp into oil, water, and solid residues.

As described above, the vegetation water is rich in water-soluble, phenolic compounds. Olive pulp extract contains about 6-9% total phenolic compounds. The structures of the phenolic compounds and their precursors detected in olive oil are shown in FIG. 7: ligstroside (I); oleuropein glucoside (II); aglycone of ligstroside (III); aglycone of oleuropein glucoside (IV); dialdehydic form of ligstroside aglycone lacking a carboxymethyl group (V); dialdehydic form of oleuropein glucoside aglycone lacking a carboxymethyl group (VI); tyrosol (VII); and hydroxytyrosol (VIII). Hydroxytyrosol comprises about 40-50% of the total phenolic compounds in the olive pulp solid extract. It will be appreciated that the composition may include one, several, or all of the phenolic compositions in varying ratios. It will further be appreciated that the vegetation water composition may be formulated to comprise a desired amount and/or ratio of any combination of the phenolic compounds. It will also be appreciated that the active ingredient may be another component of the vegetation water acting alone or in combination with one or more of the phenolic compounds present.

B. Conversion of Oleuropein to Hydroxytyrosol

In one embodiment, the composition is a hydroxytyrosol rich composition. In this embodiment, at least a portion of the oleuropein contained in the vegetation water is converted to hydroxytyrosol. In one embodiment, as described in co-owned U.S. Pat. No. 6,416,808 and U.S. Application No. 2003/0108651, the pH of the vegetation water may be decreased by the addition of acid, and the vegetation water be allowed to incubate under conditions which promote acid hydrolysis of oleuropein to hydroxytyrosol. The sample may then be fractionated or extracted to separate hydroxytyrosol from other compounds.

The acid is added to the vegetation water preferably to adjust the pH between 1 and 5, and more preferably to adjust the pH between 2 and 4. In a preferred embodiment, citric acid is used to adjust the pH of the vegetation water. Solid citric acid can be added while continuously stirring in an amount of preferably about 10 to 20 kg of acid per about 1000 liters of vegetation water. The pH of the resulting solution can be monitored, and the pH adjusted accordingly such as by addition of more acid to achieve and maintain the desired pH.

In other embodiments, the acid may be an organic or inorganic acid other than citric acid. Exemplary acids include the inorganic substances known as the mineral acids—sulfuric, nitric, hydrochloric, and phosphoric acids—and the organic compounds belonging to the carboxylic acid, sulfonic acid, and phenol (benzyl) groups. Without being limited as to theory, the addition of acid to the vegetation water appears to serve several purposes: (i) it stabilizes the vegetation water from air (oxygen) polymerization of phenolic molecules; (ii) it attenuates fermentation of the vegetation water by endogenous and/or exogenous bacteria and yeast; and (iii) it provides for the hydrolysis of oleuropein and other large phenolic molecules and conversion of such into hydroxytyrosol. In one embodiment, the mixture is allowed to incubate until hydroxytyrosol is 75-90% of the total combination of oleuropein and hydroxytyrosol. In another embodiment, substantially all of the oleuropein in the original mixture is converted to hydroxytyrosol.

C. Purification of Hydroxytyrosol

Following the conversion of oleuropein to hydroxytyrosol, the incubated vegetation water may be purified or fractionated by any suitable method known in the art. Exemplary methods of fractionation include partitioning with an organic solvent, such as ethyl acetate, chromatographic methods, including gel chromatography and high pressure liquid chromatography (HPLC), or liquid extraction with supercritical fluids such as carbon dioxide. In other embodiments, the supercritical fluid is selected from methane, ethane, propane, butane, isobutane, ethene, propene, hydrofluorocarbons, tetrafluoromethane, chlorodifluoromethane, dinitrogen monoxide, sulphur hexafluoride, ammonia, and methyl chloride. It will be appreciated that more than one supercritical fluid may be used in combination.

Prior to extraction with a supercritical fluid the vegetation water may have carriers such as maltodextran and/or polypropylene beads, added to the solution. Additional purification methods may also be used in accordance with the invention as mentioned above. HPLC isolation of hydroxytyrosol is described in Ficarra et al., 1991; Romani et al., 1999; and Tsimidou, 1992, each of which is expressly incorporated by reference herein.

In another embodiment, the solution may be dried prior or following extraction or purification of the desired polyphenol. The drying step preferably removes at least about 90%, more preferably at least about 95%, and even more preferably at least about 98% of the water from the vegetation water.

In one embodiment, vegetation water is obtained as described above and acidified to provide a solution which is rich in low molecular weight simple phenols and polyphenols, particularly hydroxytyrosol. In one embodiment, the vegetation water is selectively enriched for hydroxytyrosol without the presence of other components. Thus, the major polyphenolic component, hydroxytyrosol, is isolated or enriched from other members of the polyphenolic family, impurities, suspended solids, tannins, and other molecules contained in the vegetation water.

In yet another embodiment, the composition is comprised of substantially pure or pure hydroxytyrosol.

III. Methods of Treating Skin Inflammation

In another aspect, the invention provides simple, inexpensive, and safe methods for treating patients suffering from an inflammatory skin conditions as exemplified by psoriasis, eczema, and dermatitis. In another aspect, symptoms associated with these skin conditions such as psoriasis, eczema, and dermatitis are treated or alleviated by the method described herein. In accord with this aspect of the invention, a composition containing at least 5 mg total polyphenols obtained from vegetation water from olives is formulated into a preparation suitable for administration to a patient suffering from a skin condition such as psoriasis, eczema, or dermatitis. In another embodiment, the composition contains at least 5 mg/capsule.

In studies conducted in support of the invention, compositions comprised of the vegetation water composition were prepared and administered to test subjects, as set forth in Examples 1-6. Briefly, the pitted pulp of olives was masticated and pressed to produce a liquid-phase mixture and solid by-products. The solid by-products were separated and removed from the liquid-phase mixture by filtration and centrifugation. The liquid-phase mixture was allowed to rest to allow the oil and aqueous fractions to segregate. The aqueous phase was decanted and acidified with citric acid to adjust the pH between 2 and 4. The acidified aqueous fraction was concentrated by distillation under vacuum and dried by spray drying or oven drying under vacuum to obtain a powder, which was used to prepare the tablets as used in Examples 1-6. The formulation of the test composition tablets used in Examples 1-6 is set forth in Table 1. Each tablet contained 90 mg of olive pulp solids, 5.4 mg of total polyphenols, and ~2.5 mg of hydroxytyrosol.

In one embodiment, the composition is suitable for use in the treatment of psoriasis. Psoriasis is a chronic skin disease generally characterized by well-defined plaques that are slightly elevated and bear silvery scales, affecting about 3.35-6.5 million (Roenigk and Maibach eds. 2nd ed. New York: Marcel Dekker; 1991, pp. 213-214) in the United States with 150,000 to 260,000 new cases occurring annually (www.emedicine.com). A family association exists in one out of three cases following a multifactorial pattern. As many as seven susceptibility gene loci have been identified with PSORS1 within chromosome 6p21.3 appearing to be the most significant (Asumalahti et al., 2003). However, the susceptibility has low penetrance as only about 10% of gene carriers develop the disease (Swanbeck et al., 1997, Elder et al., 2003).

Symptoms include patches of raised red skin covered by a flaky white buildup. In certain kinds of psoriasis, symptoms include a raised, red area (pustular psoriasis) or burned (erythrodermic) appearance. Other symptoms include intense itching and burning. Some patients may have a spot or two, while others may have extensive coverage on their body. In general, symptoms are frequently found on the knees, elbows, scalp, hands, feet, or lower back. Physically, if less then 2 percent of the body is involved, the case is considered mild. Between 3 and 10 percent is considered moderate, and more than 10 percent is severe (www.psoriasis.org).

There are several different types of psoriasis with the most common form (about 80%) being plaque psoriasis. Plaque psoriasis is characterized by well-defined patches of red or inflamed raised lesions covered with silvery white scales from parakeratosis (www.psoriasis.org). Parakeratosis refers to the increased production and movement of skin cells. In normal skin, the outer layer, made up mostly of cells called keratinocytes, is replaced every 27 to 28 days with newly formed keratinocytes. With parakeratosis, this process is sped up to about 3 or 4 days. These cells are moved to the surface faster than they can be incorporated in the skin layer, thus the keratinocytes accumulate and form scaling or lesions. Other symptoms include dilated small blood vessels and inflammatory cells (www.skincarephysicians.com). Plaque psoriasis can appear on any skin surface with the knees, elbows, scalp, trunk and nails commonly affected.

Guttate psoriasis occurs most frequently in children and is characterized by numerous small, red, individual lesions usually appearing on the trunk, arms, and legs. Guttate psoriasis often appears after an upper respiratory infection advancing the theory that psoriasis may be an autoimmune disorder. Pustular psoriasis is characterized by small pustules (skin blister containing pus) and may be generalized and widespread, or may be localized, particularly to the hands and feet (palmo-plantar pustular psoriasis). Pustular psoriasis may further cycle through erythema, pustules, and scaling. Inverse psoriasis occurs on the flexural surfaces often in skin folds or creases (armpit, groin, groin, under the breast) and presents as smooth areas of skin that are red and inflamed but do not include scaling. Erythrodermic psoriasis presents as generalized, widespread erythema, redness and fine scaling (www.psoriasis.org).

Current methods of treatment include topical therapy, phototherapy, and systemic therapy. Topical therapy includes moisturizing creams and lotions, anthralin, calcipotriene, calcitriol, corticosteroids, salicylic acid, tar, and tazorotene. Phototherapy or light therapy has been used to treat psoriasis for hundreds of years (Lebwohl et al., Ann Rheum Dis, 64(Suppl. 2):ii83-ii86, 2004). Current approaches include treatment with UVB, UVA in combination with ingestion or topical application of a photosensitizing medication (PUVA), climatotherapy, and laser therapy. Systemic therapy is indicated when lesional burden is extensive and/or frequently relapsing (Ho, Br. J. Dermatol., 67:1-10, 2004). Accepted systemic therapies include methotrexate, acitretin, and cyclosporin. However, a number of patients are refractory or unresponsive to systemic treatment (Mason and Krueger, J. Am. Acad. Dermatol., 47(6): 67-72, 2001). Further, the accompanying side effects and/or toxicity of the treatments make them unsuitable for continued use. Additionally, there are a number of unconventional therapies including antibiotics, immunosuppressives such as tacrolimus, and hydroxyurea among others (Lebwohl et al., Ann Rheum Dis, 64(Suppl. 2):ii83-ii86, 2004).

It is estimated that 75% of patients with psoriasis have mild to moderate clinical severity of disease (<20% of body surface area affected or a Psoriasis Area Severity Index (PASI) score of <10) and can be satisfactorily managed on an outpatient basis with topical therapy. Yet 100% clearance of lesions is not a realistic expectation for patients treated with topical medications. Reported complete clearance rates range from 2% with tazarotene gel to 45% with a combination of 0.005% calcipotriol ointment and 0.1% betamethasone ointment. In addition, topical therapies for psoriasis have significant side effects that must be considered by both physician and patient when developing a treatment program (Bruner et al., Dermatology Online Journal 9 (1): 2, 2003).

There is currently no cure for psoriasis and the primary treatment goal is to reduce or ameliorate the symptoms associated with the disease such as to reduce the size, thickness, and extent of plaque, papules, and erythema. The measure of response to therapy (i.e., reduction in symptoms) is generally based on a physician global assessment (PGA) or psoriasis area and severity index (PASI) score. A reduction of 50 percent from pretreatment baseline scores is generally accepted as a positive physical response; a reduction of 75 percent or more is generally accepted as a superior response approaching clearance (Marchetti et al., Dermatology Online Journal 11 (1):1, 2005).

Relapse and remittance are common occurrences over the natural history of the disease. Additionally, many cases are recalcitrant or refractory to known treatments. Topical therapy produces remission in 65 to 81% of patients with remission occurring for 2.25 to 4 months with continued maintenance of therapy. Phototherapy produces remission in 62.5 to 80% of cases with remission periods from 3 to 5.5 months with continued maintenance of therapy (Marchetti et al., Dermatology Online Journal 11 (1):1, 2005).

Figures 3A, 3B:
FIGS. 3A-3F are scanned images of the shins, knees, and calves of a patient suffering from pustular psoriasis before treatment (FIGS. 3A-3B), after two months of treatment (FIGS. 3C-3D), and after three months of treatment (FIGS. 3E-3F)
Figures 3C, 3D:
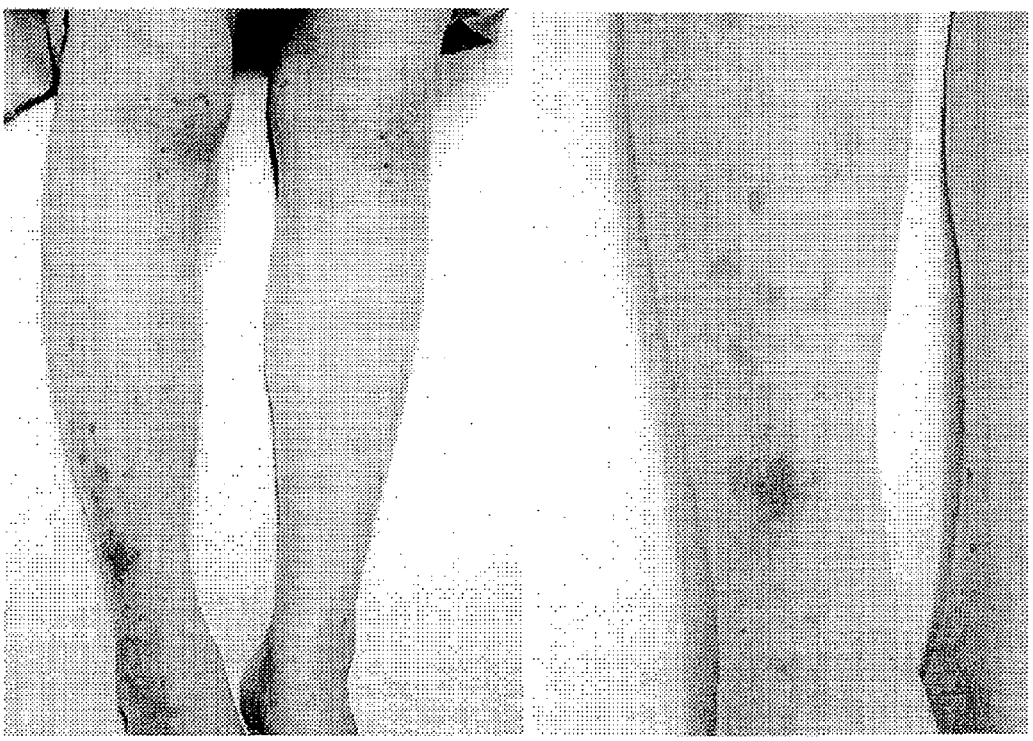
Figure 3E:

The vegetation water composition of the invention is particularly well suited for treatment of psoriasis that has proven refractory to conventional treatment, as exemplified by glucocorticoids and/or immunosuppressives. In studies conducted in support of the invention, compositions comprised of the vegetation water were prepared and administered to test subjects suffering from psoriasis, as set forth in Examples 3 and 6. The test composition was formulated as a tablet, where the formulation is set forth in Table 1. Briefly, each tablet comprised 90 mg of olive pulp formulations, 5.4 mg of total polyphenols, and 2.5 mg hydroxytyrosol. As described in Example 3, a patient suffering from purulent psoriasis on the knees and shins was treated with 2 tablets daily of the vegetation water composition. The patient had previously been refractory to treatment with antibiotics and antihistamines. FIGS. 3A-3B show the lesions on the shins, calves, and knees of the patient prior to treatment with the vegetation water composition. As seen in FIGS. 3C-3D, after two months of treatment, the severity and extent of the lesions was greatly reduced. The large, discrete lesions on the anterior of the shin were completely cleared. Coverage of the generalized lesions on the lateral shins and calves were reduced by at least 40-50%. After three months of treatment, the lesions on the shins were nearly resolved and the lesions on the knees were greatly improved (FIG. 3E). Additionally, the coverage of the lesions on the calves were at least 60-70% reduced (FIG. 3F); and the erythema was reduced in the remaining lesions.

Figure 6A:
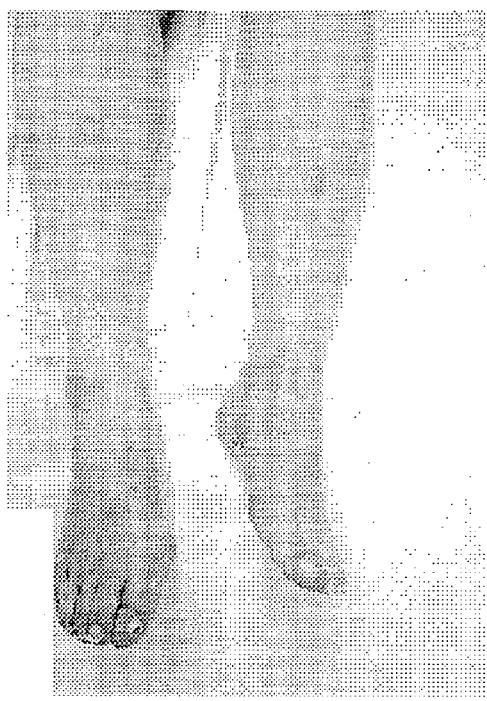
FIGS. 6A-6H are scanned images of the shins and feet of a patient suffering from pustular psoriasis and palmo-plantar pustular psoriasis before treatment (FIGS. 6A-6D) and after eight months of treatment (FIGS. 6E-6H)
Figure 6B:
Figure 6C:
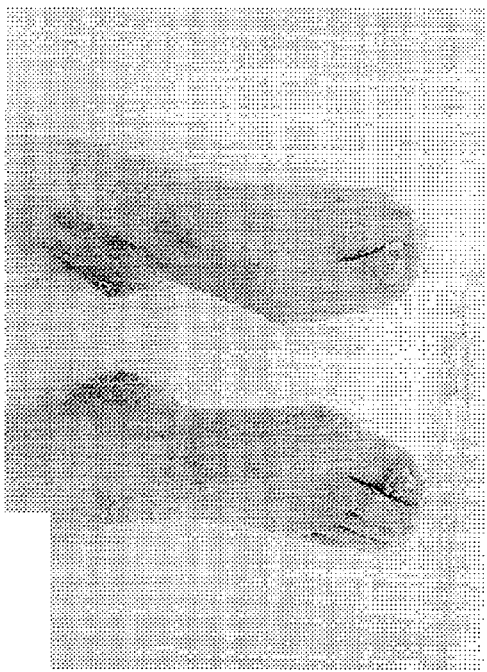
Figure 6D:
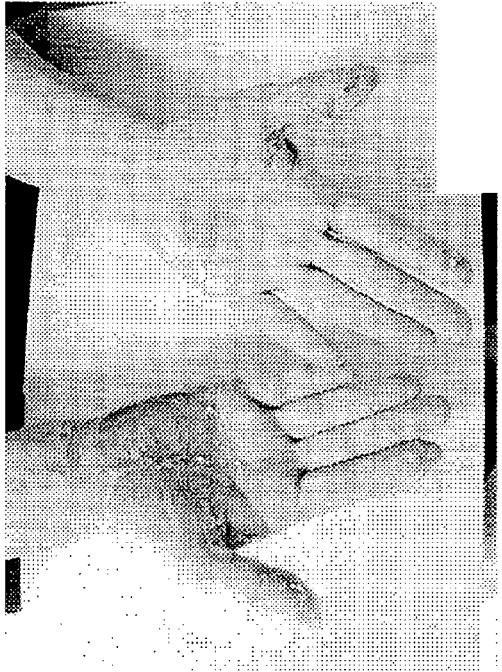
Figure 6E:
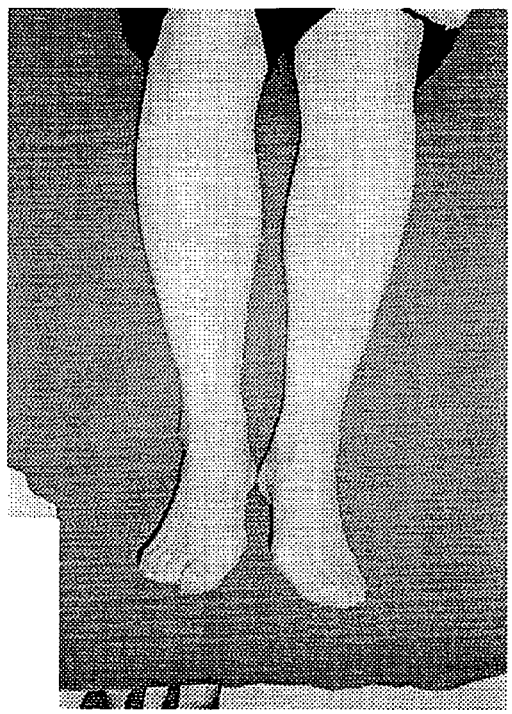
Figure 6F:
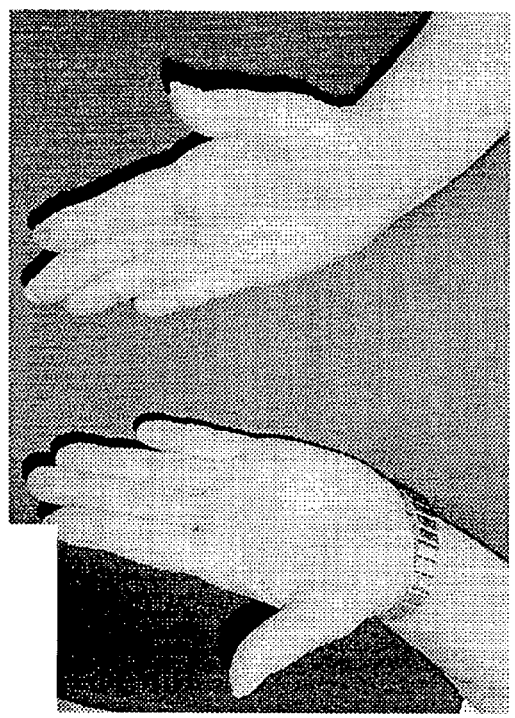
Figure 6G:
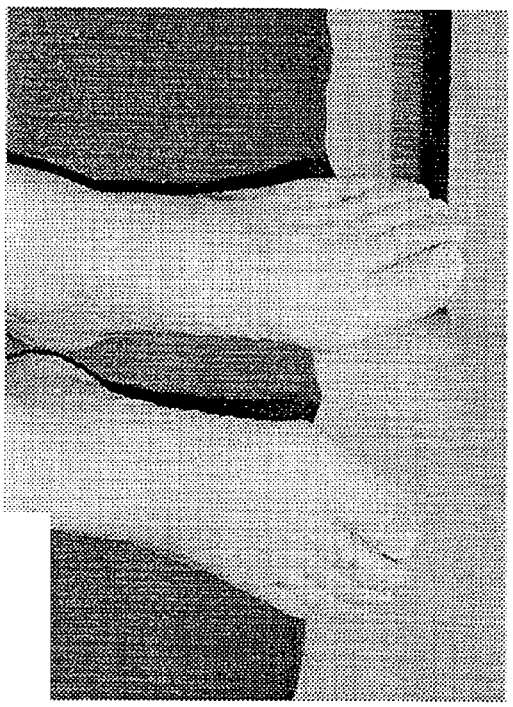
Figure 6H:
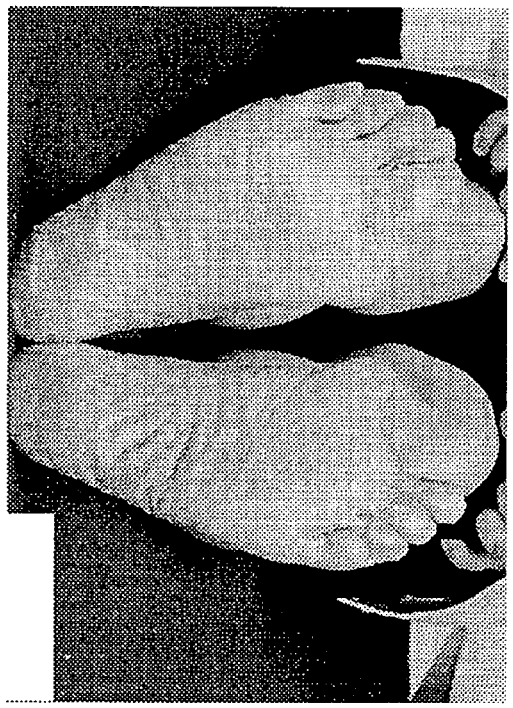

As described in Example 6, a patient suffering from palmo-plantar pustular psoriasis and generalized pustular psoriasis on the shins, feet, and ankles was treated with the vegetation water composition. The patient had formerly proven refractory to treatment with glucocorticoids and immunosuppressants after treatment for 2.5 years. As seen in FIGS. 6B and 6D, the palmo-plantar lesions covered over 90% of the soles of both feet and the palms of both hands extending over the fingers and toes to the nails. Additionally, the patient exhibited large pustules on the feet, ankles, and shins (FIGS. 6A and 6C). After two months of treatment with the vegetation water composition, the patient reported improvement in the erythema and pruritus associated with the psoriasis. The degree and coverage of the lesions had significantly improved after three months of treatment such that the dosage of the immunosuppressant was reduced by half. After eight months of treatment, the psoriasis was resolved on the shins, ankles and the top of the feet (FIG. 6E). Further, the palmo-plantar lesions were alleviated except for some residual deformation and discoloration of the toe nails (FIGS. 6F-6H).

In another embodiment, the composition is suitable for use in the treatment of eczema. Eczema involves an inflammation of the skin and appears to be an abnormal response of the body's immune system. In some types of eczema, the inflammatory response to irritating substances is overactive, causing itching and scratching. Eczema is not contagious and currently cannot be cured. Presently, treatment focuses on ameliorating the symptoms and avoiding triggers. Examples of eczema include atopic eczema, allergic contact dermatitis, irritant contact dermatitis, seborrhoeic dermatitis, varicose eczema, nummular eczema, and discoid eczema. Symptoms of eczema include dryness, flakiness, heat, blisters, and itching. In mild forms the skin is dry, hot and itchy, while in more severe forms the skin can become broken, raw and bleeding. The causes of eczema are many and varied, and depend on the particular type of eczema including heredity, allergens, irritants such as chemicals and detergents, allergens such as nickel, and yeast growths (www.medinfo.co.uk). Atopic eczema or atopic dermatitis is a chronic, superficial inflammation thought to be due to an inherited tendency toward allergy. It is common in infants and usually appears between the ages of two and eighteen months. Atopic eczema often clears up as the child ages and most outgrow the condition by puberty. Nummular eczema presents with circular, itchy, scaling patches on the skin. The cause of this eczema is unknown. Treatments include corticosteroid ointments although the condition is often resistant to treatment (*Encyclopedia of Medicine*, Clayman, Ed., Random House, NY, 1989). Allergic contact dermatitis develops when the body's immune system reacts against a substance in contact with the skin. Exemplary substances include nickel, perfumes, rubber and drugs. Seborrhoeic eczema generally affects infants under the age of one and adults between the ages of 20 and 40. It is usually seen on the scalp as mild dandruff, but can spread to the face, ears and chest. The skin may become red, inflamed and the skin may flake. The adult condition may be caused by a yeast growth and treatment with an anti-fungal cream may be necessary.

Treatments for eczema include emollients, topical and oral steroids, topical immunomodulators such as tacrolimus and pimecrolimus, UV light, and antihistamines, creams, ointments, shower and bath oils for moisturizing the skin, evening primrose oil supplements, phototherapy, immune system suppressants including cyclosporin, and antibiotics for infections resulting from eczema (www.medinfo.co.uk).

In another embodiment, the vegetation water composition of the invention is suitable for treatment of eczema, especially eczema that has been demonstrated to be resistant or refractory to conventional treatments, as exemplified by glucocorticoids, antihistamines, and/or antibiotics. In studies conducted in support of the invention, compositions comprised of the vegetation water were prepared and administered to test subjects suffering from allergic dermatitis, as set forth in Examples 2 and 4. Additionally, the vegetation water composition was prepared and administered to a test subject suffering from seborrhoeic dermatitis and lichen ruber planus as described in Example 5. The test composition was formulated as a tablet, where the formulation is set forth in Table 1. Briefly, the each tablet comprised 90 mg of olive pulp solids, 5.4 mg of total polyphenols, and 2.5 mg hydroxytyrosol.

As described in Example 2, a patient who had been prescribed digitoxin for atrial fibrillation suffered from repeated episodes of drug sensitive dermatitis in reaction to the digitoxin. The patient was prescribed an antihistamine and glucocorticoid for 2 to 3 days during outbreaks. As seen in FIGS. 2A-2B, before treatment, the digitoxin-induced dermatitis outbreaks occurred as numerous erythemic lesions on the wrists, upper forearms, and medial ankles. As seen in FIGS. 2C-2D, after only two months of treatment with the vegetation water composition, the lesions on the wrists, forearms, and ankles were completely resolved.

As described in Example 4, a patient diagnosed with allergic dermatitis of unknown cause on the forearms, wrists, and hands (FIGS. 4A-4B) was treated with the vegetation water composition. The patient was initially treated with an antihistamine and a glucocorticoid for over two years, but proved refractory to treatment. The patient was then treated with the vegetation water composition. Briefly, two tablets formulated as in Table 1 were administered orally to the patient daily. After one month of treatment with the vegetation water composition, the lesions had improved enough that the antihistamine and glucocorticoid were discontinued. After two months of treatment with the vegetation water composition, there was no visual indication of the lesions as seen in FIGS. 4C-4D. After five months of treatment, the lesions remained in remission (FIGS. 4E-4F).

Figure 5A:
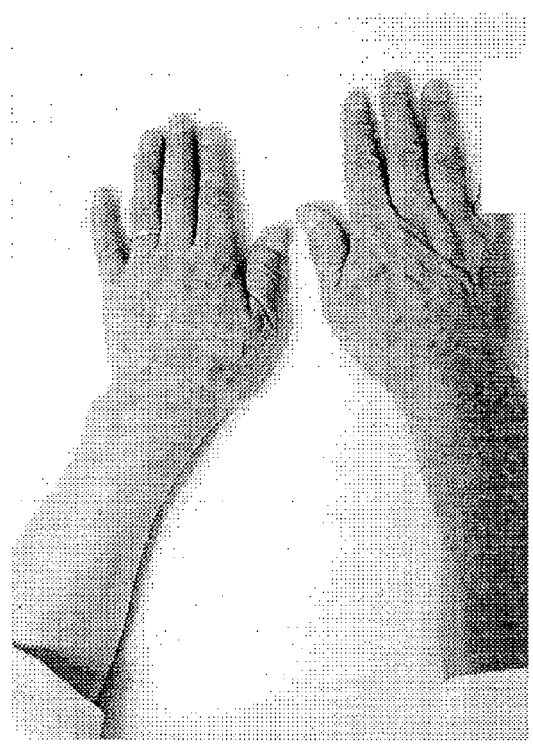
FIGS. 5A-5I are scanned images of the forearms of a patient suffering from lichen ruber planus (FIGS. 5A-5E), and the face and scalp of the same patient suffering from seborrhoeic dermatitis (FIGS. 5F-I)
Figure 5B:
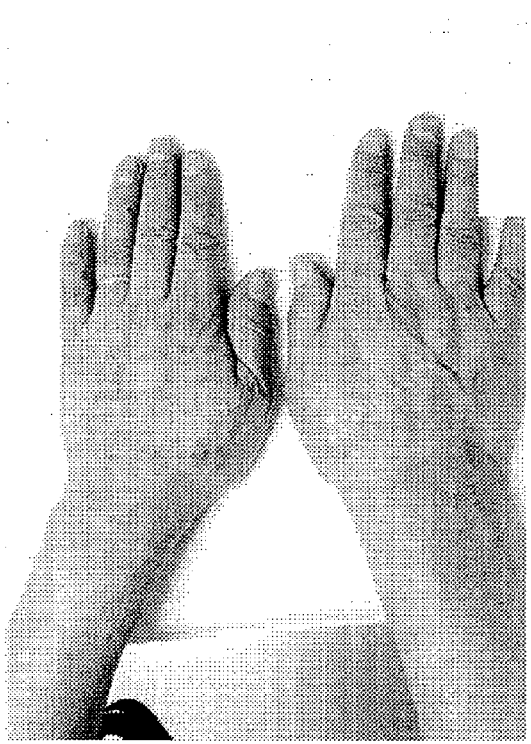
Figure 5C:
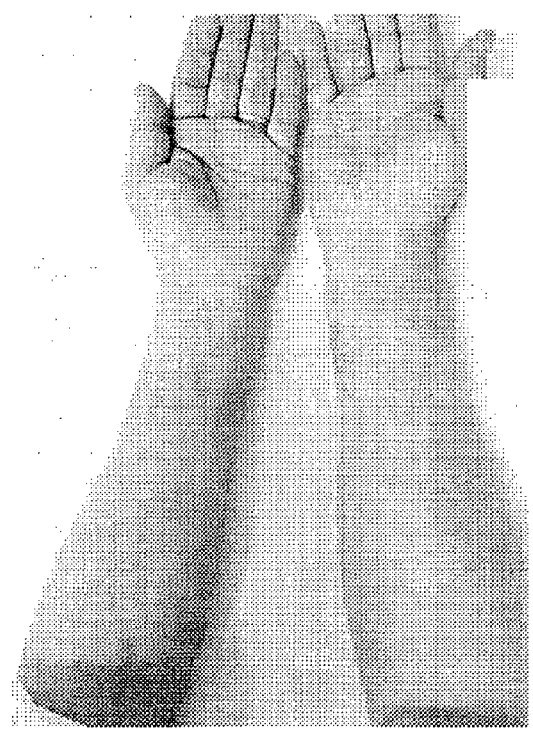
Figure 5D:
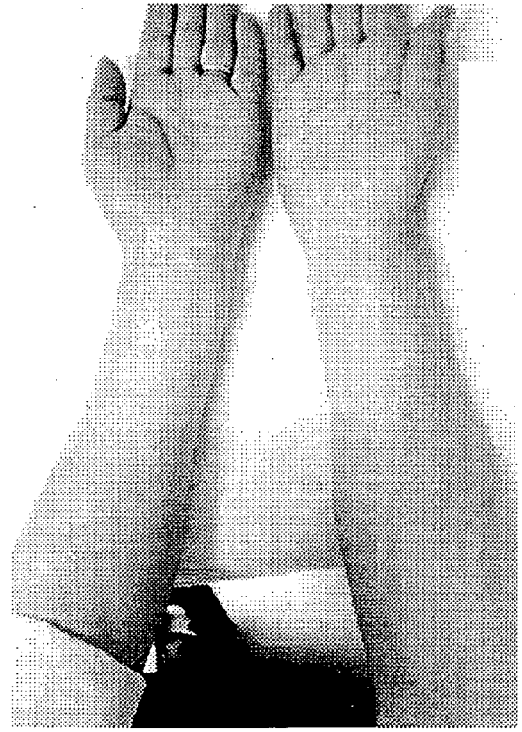
Figure 5E:
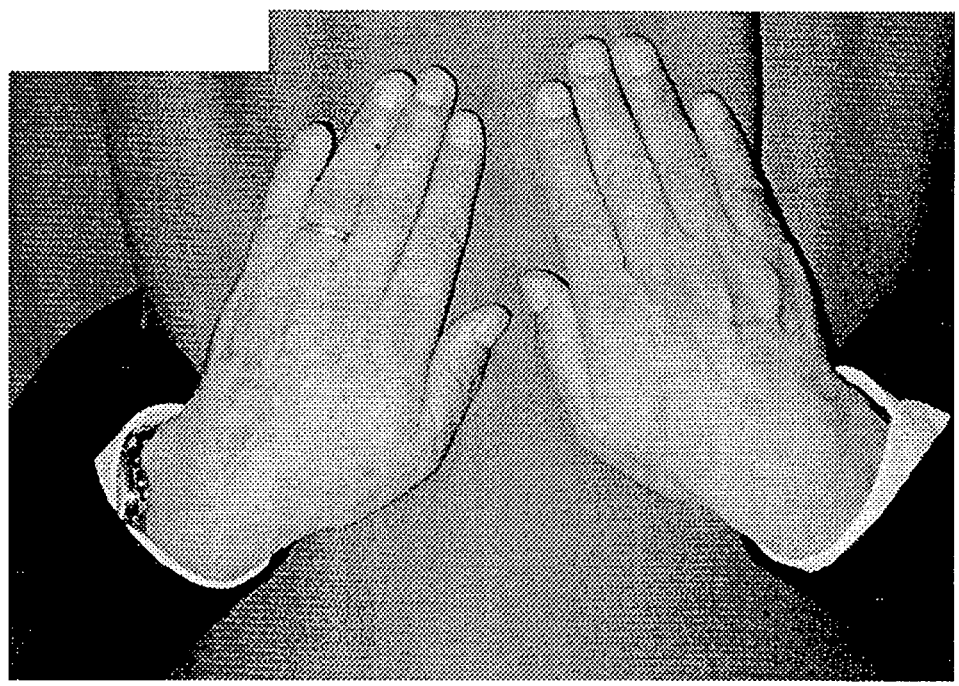
Figure 5F:
Figure 5G:
Figure 5H:
Figure 5I:

As described in Example 5, a patient diagnosed with seborrhoeic dermatitis of the scalp and lichen ruber planus on the palms and wrists was treated with the vegetation water composition. Treatment of the lichen ruber planus is described further below. Before treatment, the seborrhoeic dermatitis presented as a generalized erythema and inflammation on the scalp and forehead, see FIG. 5F. About 90% of the forehead was covered with inflamed, reddened lesions. The patient was treated with the vegetation water composition. Briefly, two tablets formulated as in Table 1 were administered orally to the patient on a daily basis. As seen in FIG. 5G, after only two months of treatment, the lesions on the forehead were nearly resolved. As seen in FIGS. 5H-5I, after 9 and 11 months of treatment, respectively, the dermatitis of the scalp had also improved as evidenced by the reduced erythema and inflammation.

Figure 1A:
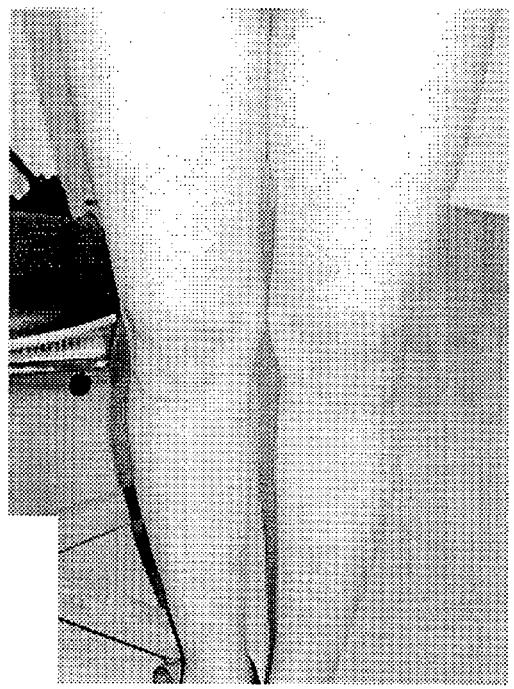
FIGS. 1A-1D are scanned images of the thighs and shins of a patient suffering from erythema nodosum before (FIGS. 1A-1B) and after treatment (FIGS. 1C-1D)
Figure 1B:
Figure 1C:
Figure 1D:
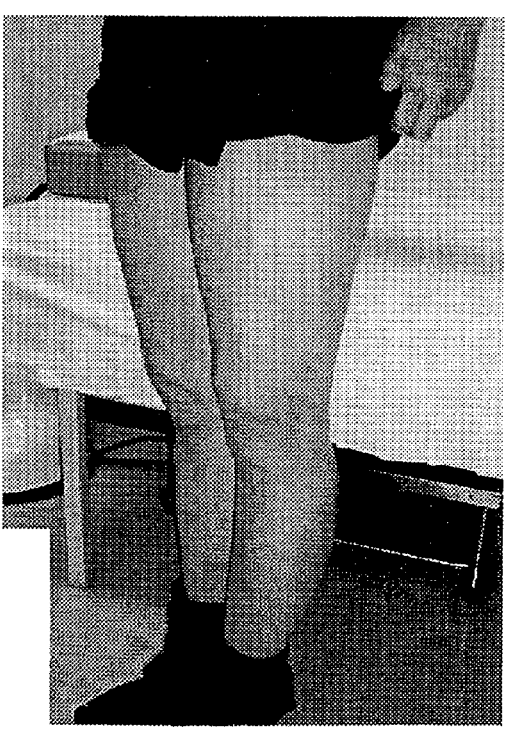

In another embodiment, the compositions of the invention are suitable for treating erythema nodosum. Erythema nodosum is an inflammatory condition characterized by tender, red bumps, and is usually found on the shins, but may also occur on other areas of the body such as the buttocks, calves, ankles, thighs, and upper extremities. Quite often, erythema nodosum is not a separate disease, but, rather, a sign of some other disease, or of sensitivity to a drug. Typical treatments include antibiotics, treatment of the underlying cause, pain relievers, and corticosteroids (www.umm.edu). As seen in Example 1, a patient suffering from erythema nodosum of unknown cause was successfully treated with the vegetation water composition. The patient had previously been refractory to treatment with predonine. As seen in FIGS. 1A-1B, the patient presented with several large (>1 inch) red lesions on the thighs, anterior and lateral shins. The patient was treated with the vegetation water composition. Briefly, two tablets formulated as in Table 1 were administered orally to the patient daily. After two months of treatment with the vegetation water composition the patient reported significant improvement in the lesions and the predonine was discontinued. After four months of treatment, the erythema nodosum was in remission. After seven months of treatment, the erythema nodosum remained in remission with no visual evidence of the lesions (FIGS. 1C-1D).

In yet another embodiment, the vegetation water composition is suitable for use in the treatment of lichen diseases including lichen ruber planus and lichen urticatus. Lichen ruber planus is an idiopathic disease that is probably an autoimmune disorder. The clinical symptoms include polygonal, flat, shiny papules and pruritus. The papules may also be pink or red in color as well as hyperpigmented brownish-red. The nails may also exhibit dystrophy. The sites of predilection include the wrists, shins, ankles of the lower extremities, sacral region, mouth, and genitals. Treatments include topical steroids such as clobetasol proprionate and betamethasone proprionate ointments, systemic steroids such as prednisone, long term antibiotics, oral antifungal agents, phototherapy, acitretin, methotrexate and hydroxychloroquine, tacrolimus ointment and pimecrolimus cream, and immune modulating drugs that inhibit calcineurin (www.dermnetnz.gov). Lichen urticatus or papular urticaria, more commonly known as "hives," is characterized by local elevated ridges (wheals) and erythema of the skin. This condition is usually triggered by allergic reactions to insect bites, sensitivity to drugs, or other environmental causes (www.webmd.com).

As described in Example 5, a patient suffering from lichen ruber planus was effectively treated with the vegetation water composition. The patient presented with extensive patches of small raised, red lesions on the top of the hands as well as lesions on the medial forearm, not shown. After two months of treatment, the erythema of the lesions had improved (FIGS. 5A-5B). After five months of treatment with the vegetation water composition, the extent and degree of the lesions had further improved (FIGS. 5C-5D). The extent of the lesions on the back of the hand and the anterior forearm was reduced by at least 30-40% and there was no visual evidence of the lesions on the posterior forearm. After 9 months of treatment, the lesions on the back of the hand were in remission with no lesions evident on visual inspection, see FIG. 5E.

In a further embodiment, the vegetation water composition is suitable for treatment of photohypersensitivity dermatitis or photo-dermatitis. A large number of biological or synthetic may sensitize a patient to sunlight exposure such that the patient develops dermatitis on areas of skin exposed to sunlight when the compounds are present in their system. Such substances include drugs like demethylechloretetracycline, sulphonamides, griseofulvin, and chlorpromazine, dyes like eosins present in some cosmetics and perfumes, tar products, compounds like psoralens, among others. This type of dermatitis is usually reversible where the dermatitis occurs only when the sensitizing compound is present in the patient's system. Photo-dermatitis presents clinically as erythema, scaling, and vesiculation along-with itching in the areas exposed to sunlight. The lesions may further present only as hyperpigmentation with or without itching (www.delhihomeo.com). Current treatments include limiting exposure to sunlight and/or the sensitizing compound as well as treatments similar to those described for eczema, above.

As mentioned above with respect to psoriasis, in many cases, inflammatory skin diseases such as psoriasis and eczema are refractory to conventional treatments, that is, show little or no improvement of symptoms with treatment. As seen in Examples 1-6, the present composition is suited for systemic treatment of refractory inflammatory skin conditions such as psoriasis, eczema, and dermatitis, among others.

It will further be appreciated that a patient may suffer from more than one inflammatory skin condition. As seen in Examples 4 and 5, the present composition is further useful for the concurrent treatment of more than one inflammatory skin condition.

A. Administration

Routes of delivery include, but are not limited to, various systemic routes, including oral and parenteral routes (intravenous, subcutaneous, intraperitoneal, and intramuscular). Administration via these routes is achieved by formulating the compositions into a suitable dosage form. Non-limiting examples include pills, tablets, capsules, suspensions, syrups, liquid drops, and the like. Preparation of such dosage forms is routine to those of skill in the art. In a preferred embodiment, the composition is administered orally.

The composition may be administered either in substantially pure form (olive pulp solids or extract) or along with a pharmaceutically acceptable carrier. In one embodiment, the composition is dissolved or dispersed in the carrier as an active ingredient and formulated according to conventional practice. The carrier may be a solid form, semi-solid or liquid material which acts as a vehicle, carrier or medium for the active ingredient. Alternatively, the carrier can be in the form of a capsule or other container to facilitate oral administration. Thus, the oral dosage forms for administration in accordance with the present invention include tablets, pills, powders, capsules, syrups, liquids, and soft or hard gelatin capsules. The carrier may be any of a variety of standard physiologically acceptable carriers employed by those of ordinary skill in the art. It will be understood that the choice of suitable physiologically acceptable carrier will vary dependent upon the chosen mode of administration.

In a preferred embodiment, the composition is administered orally to a patient suffering from an inflammatory skin condition.

It will be appreciated that the composition can further be formulated to contain various weight ratios of the phenolic compounds. In one embodiment, the composition is formulated to contain various weight ratios of hydroxytyrosol to oleuropein. In preferred embodiments, the weight ratio of hydroxytyrosol to oleuropein is between 4:1 and 200:1, preferably about 10:1, and more preferably about 100:1. The composition may also be formulated to contain a weight ratio of hydroxytyrosol to tyrosol of between about 2:1 and about 50:1, preferably between about 5:1 and about 30:1.

In one embodiment, the composition is a hydroxytyrosol rich composition. In another embodiment, the composition comprises purified hydroxytyrosol. In yet another embodiment, the composition comprises purified hydroxytyrosol in combination with a pharmaceutically suitable carrier. In a further embodiment, the composition comprises purified hydroxytyrosol administered in combination with other treatment compositions and methods.

The compositions for administration in the present invention may be formulated with other common pharmaceutically acceptable excipients, including lactose, dextrose, sucrose, sorbitol, mannitol, starches, gums, calcium silicate, microcrystalline cellulose, polyvinylpyrrolidone, methylcellulose, water, alcohol and the like. The formulations may additionally include lubricating agents such as talc, magnesium stearate and mineral oil, wetting agents, emulsifying and suspending agents, preserving agents such as methyl- and propylhydroxybenzoates, sweetening agents or flavoring agents. Further, the compositions of the present invention may be formulated so as to provide quick, sustained or delayed release of the active ingredient after administration to a subject. Sustained or delayed release may be accomplished using any known method including semi-permeable polymeric matrices in the form of shaped articles such as films or microcapsules.

Parenteral formulations for use in accordance with the present invention are prepared using standard techniques in the art. The term parenteral as used herein includes subcutaneous injections, intravenous, intramuscular, intrasternal injection, or infusion techniques. Such formulations are commonly prepared as sterile injectable solutions, using a parenterally acceptable carrier such as isotonic saline solution or as a sterile packaged powder prepared for reconstitution with sterile buffer or isotonic saline prior to administration to a subject.

In one embodiment, the composition may be administered at regular intervals, e.g., daily, two times daily, or three times daily. In another embodiment, the composition is administered over a period of time, e.g. 1 to 12 months or more. It will be appreciated that administration of the composition may be continued for an indefinite time period. It will be appreciated that dosages of the composition will vary dependent upon the compound used in the composition. Preferred doses for oral administration of the composition include (i) from about 90-360 mg of solid olive pulp solids and/or extract on a daily basis, with specific embodiments of 90, 180, 270, and 360 mg of solid olive pulp dry formulation contemplated, (ii) from about 5-22 mg total simple phenols and polyphenols on a daily basis, with specific embodiments of 5, 5.4, 10, 10.8, 16, 16.2, 21.6, or 22 mg contemplated, (iii) from about 2.5-10 mg hydroxytyrosol on a daily basis, with specific embodiments of 2.5, 5, 7.5, and 10 mg contemplated. In other embodiments, up to 2 g/kg is orally administered, or (iv) from about 10-20 mg of the composition per dose.

Dosages will vary in accordance with such factors as the age, health, sex, size and weight of the patient, the route of administration, and the efficacy of the compound. Greater or lesser amounts of the compound may be administered as required.

It will be appreciated that other components or active ingredients may be administered in combination with the treatment compound. It will further be appreciated that other treatment methods may be used in combination with administration of the treatment compound.

From the foregoing, it can be seen how various objects and features of the invention are met. Those skilled in the art can now appreciate from the foregoing description that the broad teachings of the present invention can be implemented in a variety of forms. It will be appreciated that embodiments and subgroups described herein may be combined in the method and composition. Therefore, while this invention has been described in connection with particular embodiments and examples thereof, the true scope of the invention should not be so limited. Various changes and modification may be made without departing from the scope of the invention, as defined by the appended claims.

The following examples illustrate methods of treating inflammatory skin conditions with compositions from vegetation water from olives in accordance with the invention. The examples are intended to illustrate, but in no way limit, the scope of the invention.

III. Examples

Preparation of Treatment Composition

Tablets were formulated with a composition obtained from vegetation water from olives as in Table 1.

TABLE 1

Tablet formulation

| Ingredient | mg/tablet |
| --- | --- |
| olive pulp extract (solids) | 90 |
| citric acid | 15 |
| maltodextrin | 205 |
| silicon dioxide | 10 |
| magnesium stearate | 10 |
| modified cellulose | 60 |
| dicalcium phosphate | 600 |
| stearic acid | 70 |
| Total | 1060 |

Each tablet contained 90 mg of olive pulp extract (solids), 5.4 mg total polyphenols and ~2.5 mg hydroxytyrosol.

Example 1

A 45 year-old female was diagnosed with erythema nodosum and presented with lesions>1 inch on the left thigh anterior and the medial knee of both legs, as well as several smaller lesions<1 inch on the thighs and upper calves and shins (FIGS. 1A-1B). The patient had been treated with 5 mg predonine for nearly 2.3 years with little resolution.

The patient was treated with two tablets comprising the vegetation water composition daily. After two months of treatment with the vegetation water composition, the predonine was discontinued. After four months of treatment, the patient showed no visual evidence of the erythema nodosum on the thighs, knees, or lower legs. After 11 months of treatment, the patient continued to show no visual sign of the erythema (FIGS. 1C-1D).

Example 2

A 71 year-old male was diagnosed with recurring allergic dermatitis in response to digitoxin prescribed for atrial fibrillation. The dermatitis presented with generalized, erythematous lesions on the anterior wrist, forearm, and the medial ankle (FIGS. 2A-2B). The patient was treated with antihistamine and glucocorticoids for 2-3 days during outbreaks for 2.4 years.

The patient was subsequently treated with two tablets of the vegetation water composition daily. After two months of treatment, the patient showed a substantial improvement with nearly no visual evidence of the lesions (FIG. 2C-2D).

Example 3

A 70 year-old female was diagnosed with psoriasis purulenta (pustular psoriasis with purulent lesions) and presented with extensive pustules on the knees, shins, calves, ankles, and anterior of the foot (FIGS. 3A-3B) and had been suffering from psoriasis for two years. The patient had been treated with antibiotics, diuretics, and antihistamines, but proved refractory to treatment.

Figure 3F:
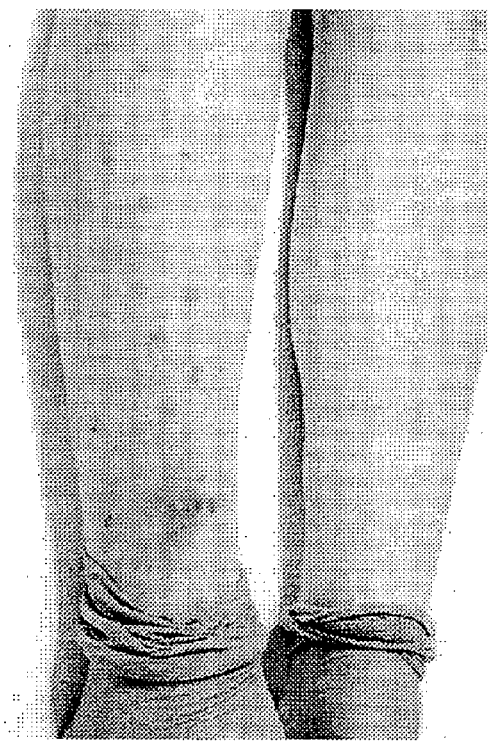

The patient was then treated with two tablets of the vegetation water composition daily. After two months of treatment, the patient exhibited a decrease in the number and size of the pustules, especially on the anterior shin and lateral calves (FIGS. 3C-3D). After three months of treatment, the patient exhibited a substantial improvement in the condition with nearly complete resolution of the lesions (FIGS. 3E-3F).

Example 4

Figure 4A:
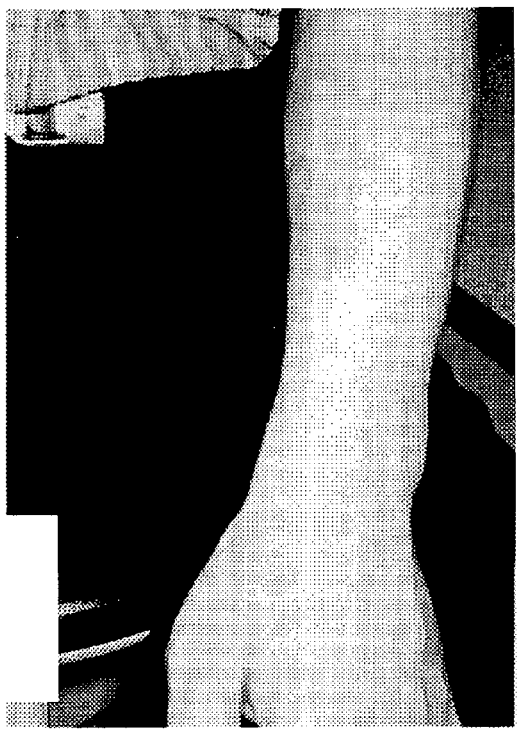
FIGS. 4A-4F are scanned images of the forearms of a patient suffering from allergic dermatitis before treatment (FIGS. 4A-4B), after two months of treatment (FIGS. 4C-4D), and after five months of treatment (FIGS. 4E-4F)
Figure 4B:
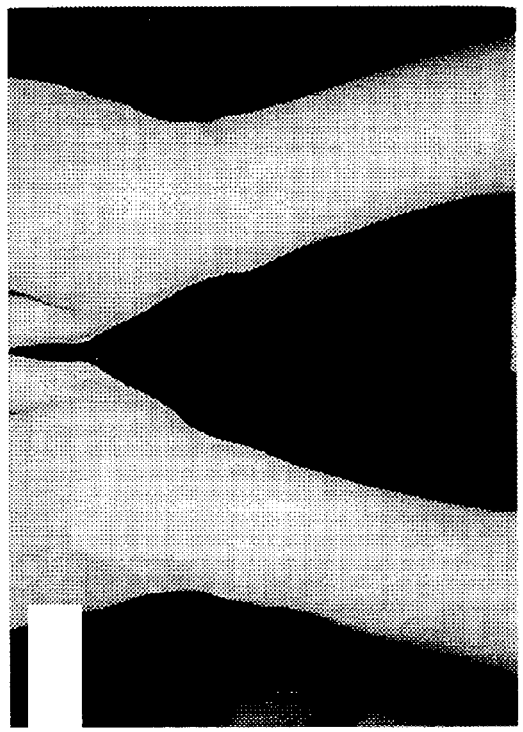
Figure 4C:
Figure 4D:
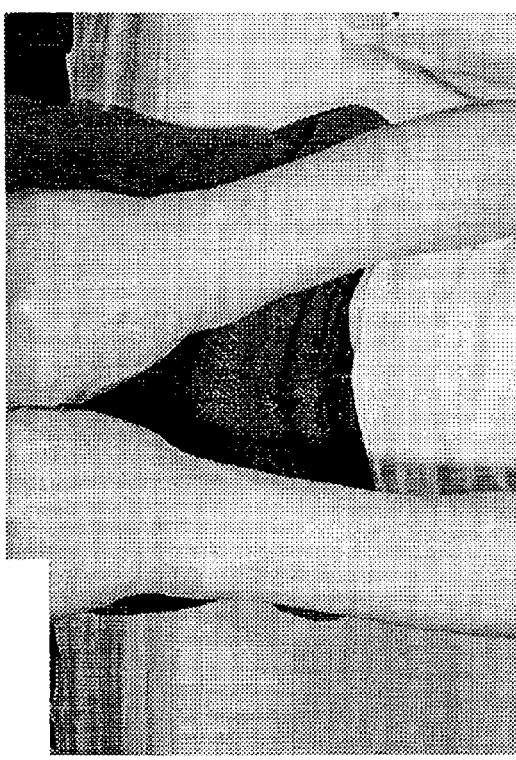
Figure 4E:
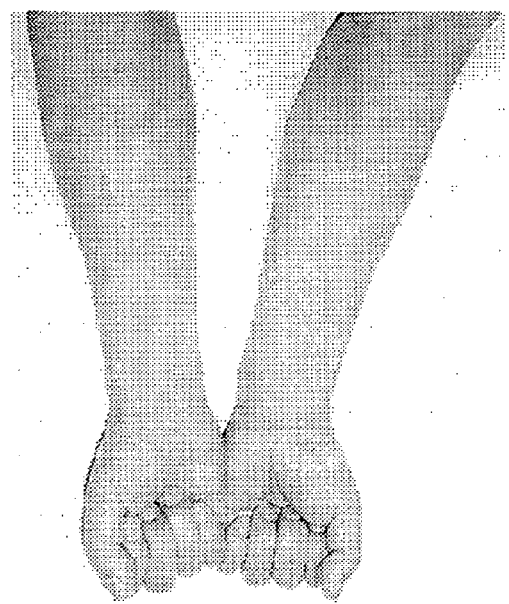
Figure 4F:
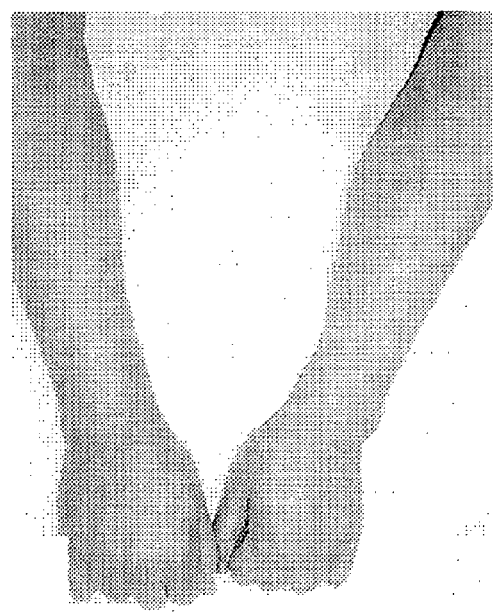

A 76 year-old male was diagnosed with allergic dermatitis and lichen urticatus as an additional diagnosis, and presented with large, >1 inch, erythematous, raised lesions on the forearms, wrists, and hands (FIGS. 4A-4B). The patient was treated with antihistamines and glucocorticoids for nearly 2 years with little or no resolution in the lesions.

The patient was refractory to treatment with the antihistamines and glucocorticoids and therefore treatment with the vegetation water composition was initiated. The patient was treated with two tablets of the vegetation water composition daily in combination with the antihistamine. After one month of treatment with the composition, the antihistamine was discontinued. After two months of treatment with the composition, the patient showed a significant reduction in lesions (at least 80% of the lesions were resolved) (FIGS. 4C-4D). After three months of treatment, the patient showed no visual evidence of lesions. After seven months of treatment, the patient remained in remission and continued to show no visual evidence of the dermatitis (FIGS. 4E-4F).

Example 5

A 66 year-old male was diagnosed with lichenoid dermatitis, allergic dermatitis, and photohypersensitivity dermatitis. The patient presented with seborrhoeic dermatitis on the forehead and at the hairline and lichen ruber planus on the palms and the wrists. The lichen ruber planus presented with localized pruritic, papular eruptions on the extensor surface of the hand and the wrists. The patient also presented with seborrhoeic dermatitis (eczema) on the scalp and forehead consisting of scaling over erythematous, raised lesions (FIG. 5F).

The patient was treated with an anti-hyperlipidemic for hyperlipidemia and an antihypertensive for 10 years. The patient was subsequently treated with a vasodilating drug for angina pectoris.

The patient was treated with two capsules or tablets of the vegetation water composition daily for the hyperlipidemia.

1. Seborrhoeic Dermatitis

After two months of treatment, a substantial improvement in the condition was noted on the forehead, which had nearly completely resolved (FIG. 5G). After nine months of treatment, the erythematousness of the lesions on the scalp was reduced (FIG. 5H). After eleven months of treatment, the lesions on the scalp were nearly resolved (FIG. 5I).

2. Lichen Ruber Planus

After two months of treatment with the composition, the patient noted a decrease in the extent of the eruptions (FIGS. 5A and 5C). After five months of treatment, the patient showed a significant reduction in eruptions and redness (at least 50% of the lesions were resolved) (FIGS. 5B and 5D). After nine months of treatment, the lichen ruber planus on the hands was completely resolved (FIG. 5E).

Example 6

A 61 year-old female was diagnosed with collagen disease and pustular psoriasis. The patient presented with localized palmo-plantar pustulosis on the extensor and flexor surface of the hands (palm) and feet (soles) exhibiting extensive, large >1 inch pustules. The patient was also exhibited acropustulosis of the phalanges (fingers and toes) with deformation, oncholysis and discoloration of the phalanx nails. Additionally, the patient was diagnosed with generalized pustular psoriasis with erythema of the feet, ankles and anterior shins (FIGS. 6A-6D). The patient was initially treated with glucocorticoids and a first immunosuppressant with no improvement.

The patient was refractory to treatment with the immunosuppressant and glucocorticoids and therefore treatment with the vegetation water composition was initiated. The patient was treated with two capsules/tablets of the vegetation water composition daily as well as a second immunosuppressant. After two months of treatment, the patient reported improvement in the extent and severity of the lesions. The dosage of the immunosuppressant was reduced after three months of treatment with the vegetation water composition. After eight months of treatment with the composition, the patient showed a significant reduction in lesions on the soles of the feet (at least 80% of the lesions were resolved) and remission of the psoriasis on the palms (FIGS. 6F-6H). Additionally, acropustulosis of the finger nails was nearly resolved, and the toe nails were significantly improved. The generalized pustular psoriasis on the feet, ankles and anterior shins was resolved (FIG. 6E).

Although the invention has been described with respect to particular embodiments, it will be apparent to those skilled in the art that various changes and modifications can be made without departing from the invention.

It is claimed:

1. A method for treating a person suffering from an inflammatory skin condition presenting as a discrete or generalized area of skin lesions, comprising:
    identifying a person suffering from such an inflammatory skin condition that has proven refractory to treatment with immunosuppressives or glucocorticoids, and
    orally administering to said person, an effective amount of a pharmaceutical composition selectively enriched for hydroxytyrosol, whereby the pharmaceutical composition is produced by (i) obtaining vegetation water from olives, (ii) adding acid to the vegetation water thereby producing acidified vegetation water, (iii) incubating the acidified vegetation water for a period until the weight ratio of hydroxytyrosol to oleuropein is between 4:1 and 200:1, thereby producing incubated acidified vegetation water, and (iv) adding 90 to 360 mg of solid olive extract to the incubated acidified vegetation water thereby producing the pharmaceutical composition, wherein the pharmaceutical composition is orally administered on a daily basis over a period of at least three months so as to reduce the area of the discrete or generalized skin lesions by at least 60%.

2. The method of claim 1, wherein the acidified vegetation water is incubated for a period until the weight ratio of hydroxytyrosol to oleuropein in the composition is between about 5:1 to 50:1.

3. The method of claim 1, wherein said oral administration comprises orally administering said composition in tablet, capsule, or pill form.

4. The method of claim 1, wherein said oral administration comprises orally administering said composition in liquid form.

5. The method of claim 1, wherein the inflammatory skin condition is refractory psoriasis.

6. The method of claim 1, wherein the inflammatory skin condition is refractory eczema.

7. The method of claim 1, wherein the inflammatory skin condition is refractory allergic dermatitis.

8. The method of claim 1, wherein the inflammatory skin condition is refractory photohypersensitivity dermatosis.

9. The method of claim 1, wherein the inflammatory skin condition is refractory lichen urticatus.

10. The method of claim 1, wherein the composition is administered at a dosage effective to deliver between about 5.4 to 10.8 mg of total polyphenols daily.

11. The method of claim 1, wherein the composition is administered at a dosage effective to deliver between about 2.5 to 5 mg of hydroxytyrosol daily.

12. The method of claim 1, wherein the immunosuppressive are selected from the group consisting of tacrolimus and hydroxyurea.

* * * * *

UNITED STATES PATENT AND TRADEMARK OFFICE
CERTIFICATE OF CORRECTION

PATENT NO. : 9,789,149 B2
APPLICATION NO. : 11/185246
DATED : October 17, 2017
INVENTOR(S) : Fujio Numano et al.

Page 1 of 1

It is certified that error appears in the above-identified patent and that said Letters Patent is hereby corrected as shown below:

In the Claims

Column 16, Line 59, delete the text "the" and insert the text -- a --

Signed and Sealed this
Tenth Day of July, 2018

Andrei Iancu
*Director of the United States Patent and Trademark Office*